US012343001B2

(12) United States Patent
Stiefferman et al.

(10) Patent No.: US 12,343,001 B2
(45) Date of Patent: Jul. 1, 2025

(54) TISSUE RETRACTOR AND ADAPTOR THEREFOR

(71) Applicant: CoreLink, LLC, St. Louis, MO (US)

(72) Inventors: Tim Stiefferman, House Springs, MO (US); Brett Smith, St. Louis (MO); Adam MacMillan, Quincy, MA (US)

(73) Assignee: CoreLink, LLC, St. Louis, MO (US)

( * ) Notice: Subject to any disclaimer, the term of this patent is extended or adjusted under 35 U.S.C. 154(b) by 0 days.

(21) Appl. No.: 17/806,651

(22) Filed: Jun. 13, 2022

(65) Prior Publication Data

US 2022/0401092 A1 Dec. 22, 2022

Related U.S. Application Data

(60) Provisional application No. 63/209,713, filed on Jun. 11, 2021.

(51) Int. Cl.
*A61B 17/02* (2006.01)
*A61B 17/00* (2006.01)

(52) U.S. Cl.
CPC ..... *A61B 17/0206* (2013.01); *A61B 2017/00407* (2013.01); *A61B 2017/00473* (2013.01)

(58) Field of Classification Search
CPC ........ A61B 17/0206; A61B 2017/0256; A61B 17/025; Y10T 403/595; F16B 2/185; B25G 3/00; B25G 3/02; B25G 3/12; B25G 3/14; B25G 3/16; B25G 3/18
USPC ....... 600/208, 210, 215, 219, 222, 224, 225, 600/226, 227, 228, 234
See application file for complete search history.

(56) References Cited

U.S. PATENT DOCUMENTS

| | | | |
|---|---|---|---|
| 6,945,933 B2 | 9/2005 | Branch et al. |
| 7,819,801 B2 | 10/2010 | Miles et al. |
| 7,850,608 B2 | 12/2010 | Hamada |
| 7,935,053 B2 | 5/2011 | Karpowicz et al. |
| 8,152,720 B2 | 4/2012 | Loftus et al. |
| 8,202,216 B2 | 6/2012 | Melkent et al. |
| 8,449,463 B2 | 5/2013 | Nunley et al. |
| 8,852,089 B2 | 10/2014 | Blackwell et al. |
| 8,882,661 B2 | 11/2014 | Hutton et al. |
| 8,968,363 B2 | 3/2015 | Weiman et al. |
| 8,992,425 B2 | 3/2015 | Karpowicz et al. |
| 9,131,935 B2 | 9/2015 | Hamada et al. |
| 9,168,132 B2 | 10/2015 | Thill et al. |
| 9,186,132 B2 | 11/2015 | Nunley et al. |
| 9,192,367 B2 | 11/2015 | Nunley et al. |
| 9,220,491 B2 | 12/2015 | Nunley et al. |
| 9,380,932 B1 | 7/2016 | Lynn et al. |
| 9,549,723 B2 | 1/2017 | Hynes et al. |
| 9,649,101 B2 | 5/2017 | Karpowicz et al. |
| 9,693,762 B2 | 7/2017 | Reimels |
| 9,737,288 B2 | 8/2017 | Karpowicz et al. |
| 9,782,158 B2 | 10/2017 | Nunley et al. |
| 9,861,273 B2 | 1/2018 | Weiman |
| 10,039,539 B2 | 8/2018 | Friedrich et al. |
| 10,172,515 B2 | 1/2019 | Lee et al. |

(Continued)

*Primary Examiner* — Eduardo C Robert
*Assistant Examiner* — David C Comstock
(74) *Attorney, Agent, or Firm* — Stinson LLP

(57) ABSTRACT

A retractor for spine surgery includes a body. Left, right, and center retracting arms are coupled to the body. Left, right, and center blades are operatively coupled to proximal ends of the respective retracting arms. A retractor adaptor is configured to couple the retractor to a mount.

13 Claims, 27 Drawing Sheets

(56) References Cited

U.S. PATENT DOCUMENTS

| | | |
|---|---|---|
| 10,172,525 B2 | 1/2019 | Davis et al. |
| 10,285,680 B2 | 5/2019 | Friedrich et al. |
| 10,357,233 B2 | 7/2019 | Miles et al. |
| 2011/0130793 A1* | 6/2011 | Woolley ............. A61B 17/7076 606/279 |
| 2012/0265177 A1* | 10/2012 | Beedall ................ A61B 17/162 606/1 |
| 2014/0135584 A1* | 5/2014 | Lee .................... A61N 1/36017 600/219 |
| 2014/0148652 A1* | 5/2014 | Weiman ............. A61B 17/3421 600/219 |
| 2014/0203550 A1* | 7/2014 | Utsch .................... F16L 23/036 285/308 |
| 2017/0150956 A1* | 6/2017 | Baudouin .......... A61B 17/0206 |
| 2019/0083081 A1 | 3/2019 | Ortiz |
| 2021/0228196 A1* | 7/2021 | Theofilos ............... A61B 17/02 |

* cited by examiner ived reference characters indicate corresponding parts throughout the drawings. -->
TISSUE RETRACTOR AND ADAPTOR THEREFOR

CROSS-REFERENCE TO RELATED APPLICATIONS

The present application claims priority to U.S. Provisional Ser. No. 63/209,713, filed Jun. 11, 2021, the entirety of which is hereby incorporated by reference.

FIELD OF THE DISCLOSURE

The present disclosure generally relates to a tissue retractor and an adaptor for attaching the tissue retractor to a retractor holder.

BACKGROUND OF THE DISCLOSURE

Tissue retractors are used in surgical procedures to provide an opening or access to a surgical site, such as a spine or other surgical site. The opening created by the tissue retractor enables a surgeon to insert surgical instruments and implants, for example, into the patient's body.

SUMMARY

In one aspect, a retractor for spine surgery generally comprises: a body; left, right, and center retracting arms coupled to the body; and left, right, and center blades operatively coupled to proximal ends of the respective retracting arms.

In another aspect, a retractor adaptor configured to couple to a tissue retractor for spine surgery generally comprises: an adaptor body having proximal and distal ends, the proximal end of the adaptor body configured to couple to an arm mount; an annular row of teeth at the distal end of the adaptor body configured to mesh with an annular row of teeth of an adaptor mount of the tissue retractor; and a latch configured to releasably latch the retractor adaptor on the adaptor mount.

BRIEF DESCRIPTION OF THE DRAWINGS

Corresponding reference characters indicate corresponding parts throughout the drawings.

DETAILED DESCRIPTION OF THE DISCLOSURE

Figure 1:
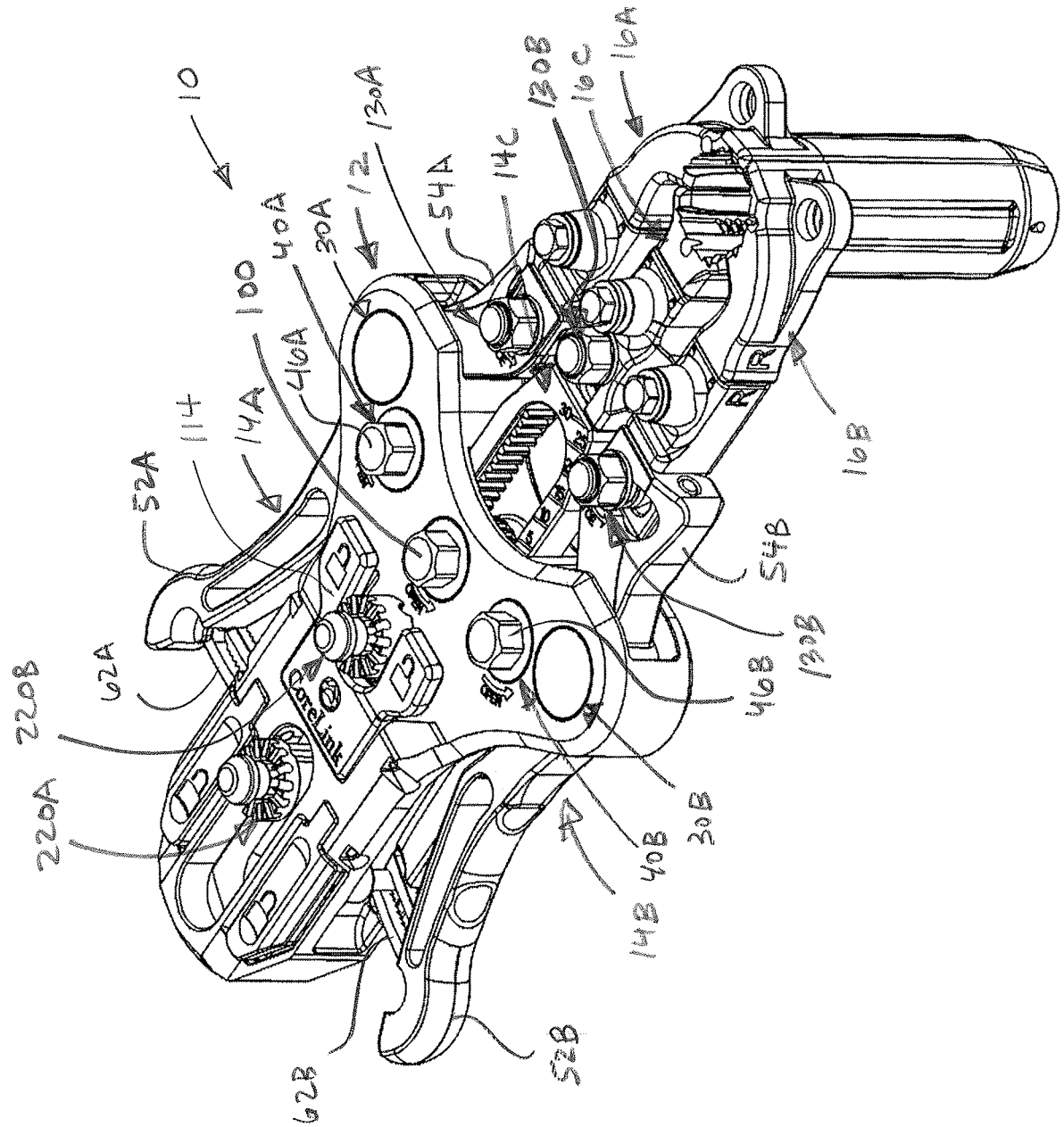
FIG. 1 is a perspective of a retractor shown in a closed, non-toed configuration.
Figure 2:
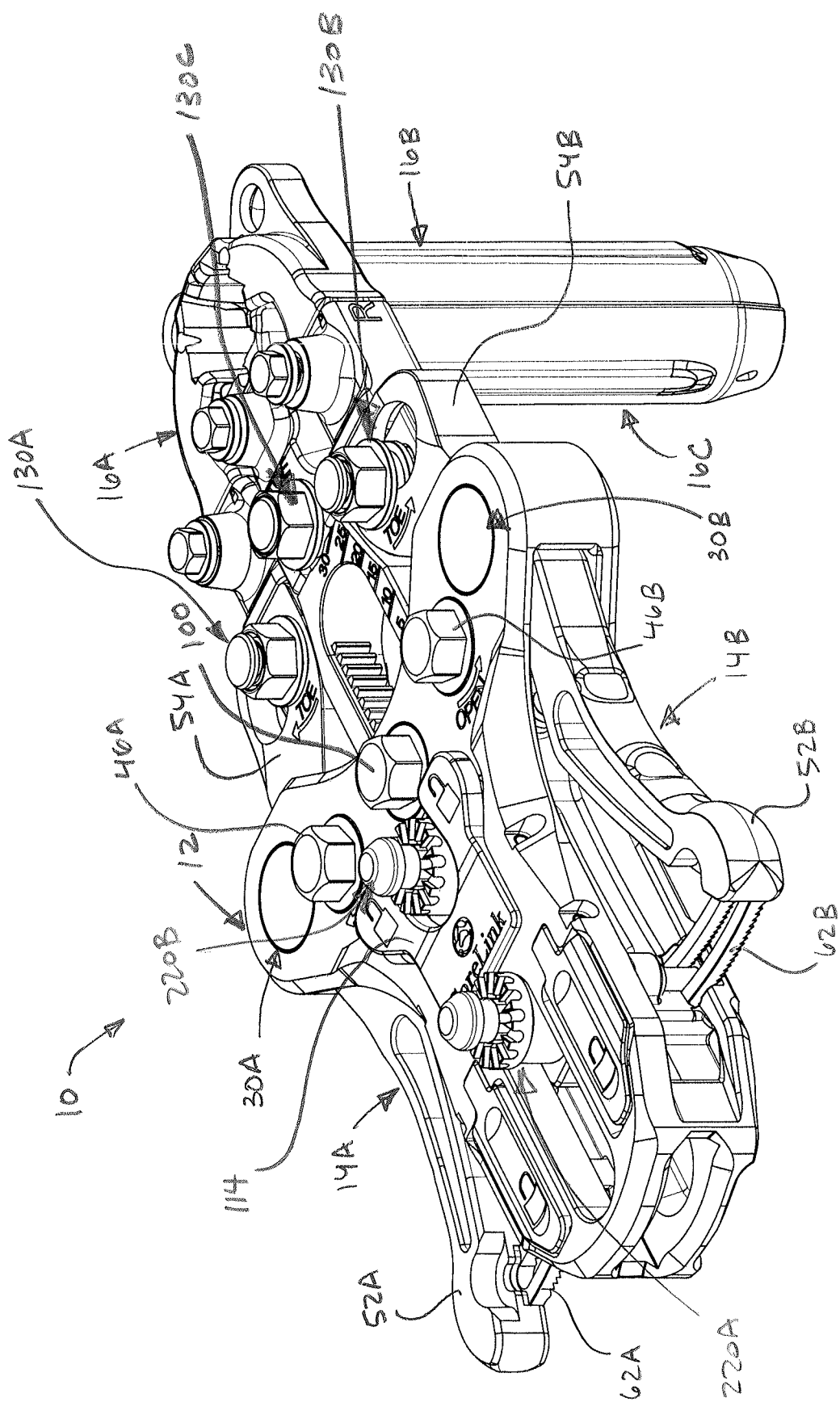
FIG. 2 is a rear perspective of the retractor of FIG. 1.
Figure 3:
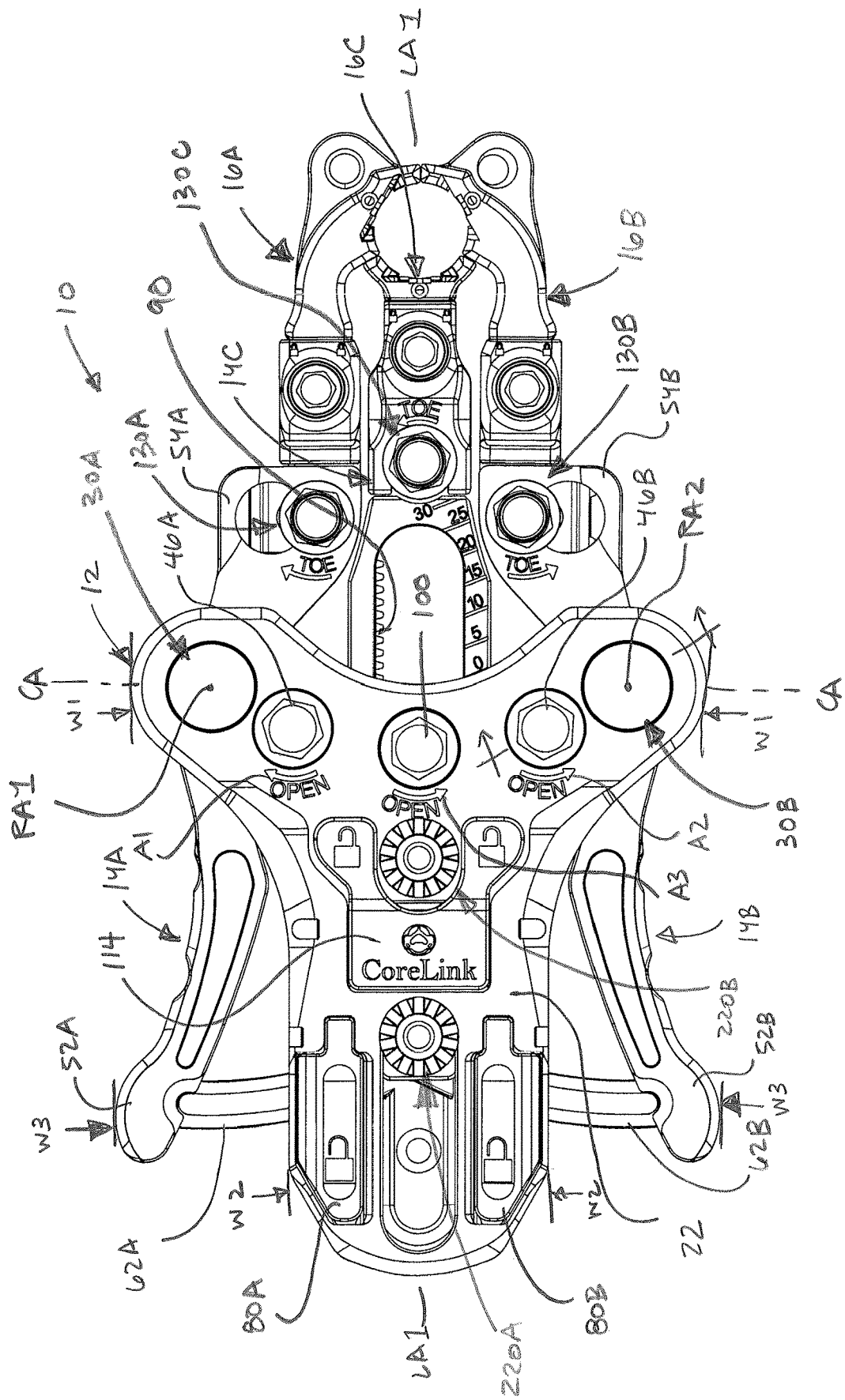
FIG. 3 top plan view of the retractor of FIG. 1.
Figure 4:
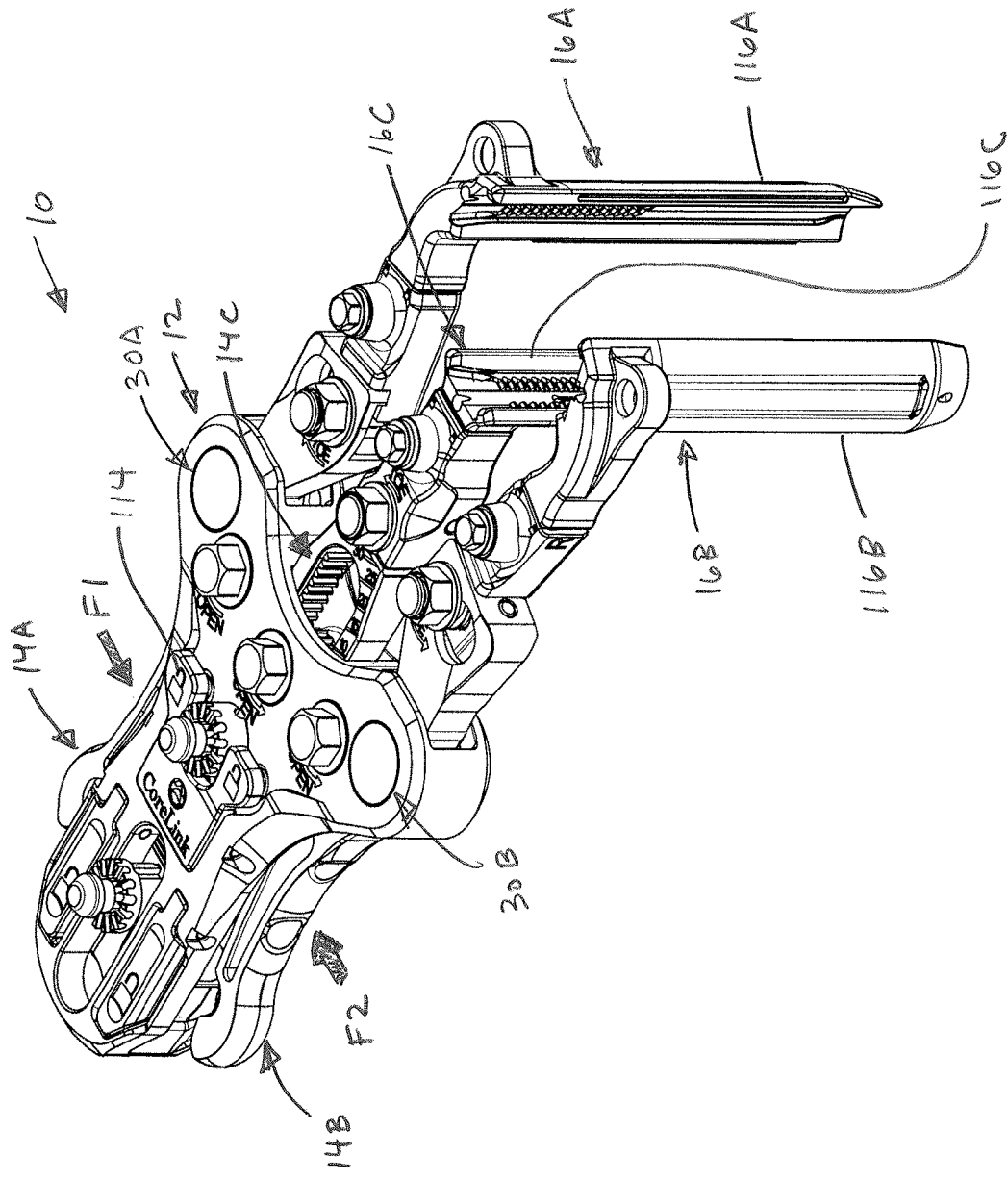
FIG. 4 is a perspective of the retractor shown in an open, non-toed configuration.
Figure 5:
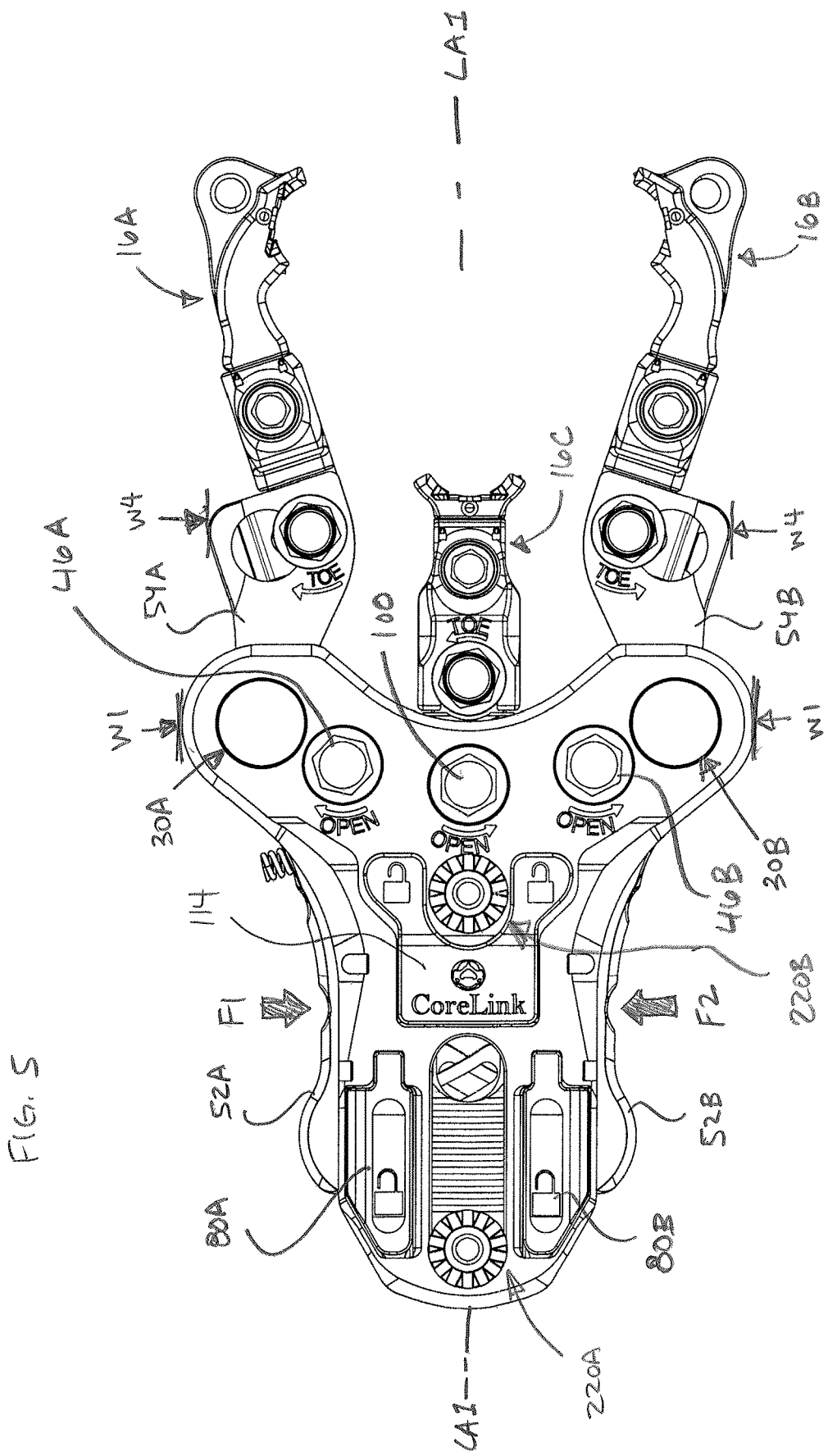
FIG. 5 is a top plan view of the retractor of FIG. 4.
Figure 6:
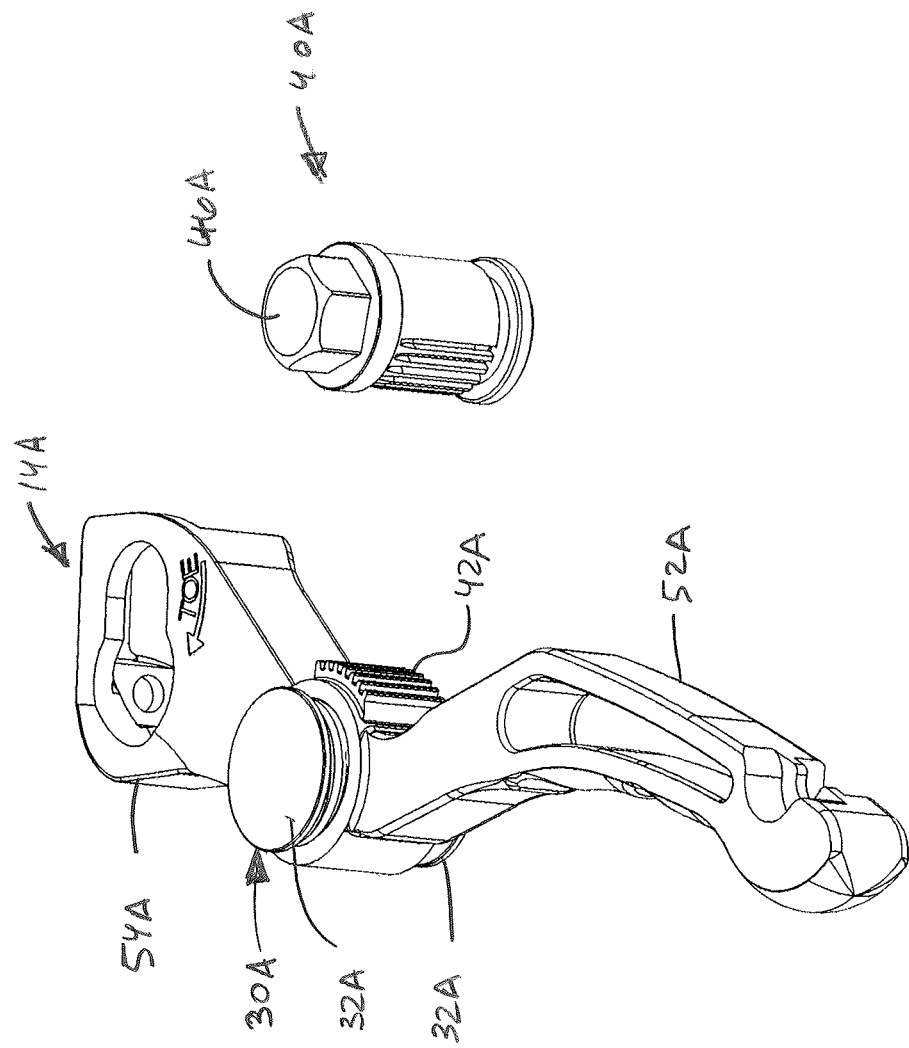
FIG. 6 is an exploded view of a left arm and an associated pinion of the retractor.

Referring now to the drawings, an illustrated embodiment of a tissue retractor constructed according to the teachings of the present disclosure is generally indicated at reference numeral 10. The tissue retractor 10 is operable to retract tissue during a surgical procedure, such as spinal surgery including but not limited to direct lateral access spine surgery (known as DLIF). The tissue retractor 10 has proximal and distal ends and a longitudinal axis LA1 (FIG. 3) extending between the proximal and distal ends. In general, the tissue retractor 10 includes a body, generally indicated at 12; left, right, and center retracting arms, generally indicated at 14A, 14B, and 14C, respectively, coupled to the body; and left, right, and center blades, generally indicated at 16A, 16B, and 16C, respectively, operatively coupled to proximal ends of the corresponding arms 14A, 14B, and 14C. In FIGS. 1-3, for example, the tissue retractor 10 is shown in its closed, non-toed configuration. In this configuration, the blades 16A, 16B, 16C are generally brought together circumferentially to form an elongate tube to enable insertion of the blades into an opening formed in the tissue to be retraced. In FIGS. 4 and 5, the tissue retractor 10 is shown in its open, non-toed configuration. In this configuration, the blades 16A, 16B, 16C are moved away from one another to thereby enable retraction of tissue. In FIG. 6, the tissue retractor 10 is shown in its expanded, toed configuration. In this configuration, the blades 16A, 16B, 16C are toed or canted to move distal ends of the blades further away from one another to thereby enable further retraction of tissue. The tissue-retractor 10 is operable between the different configurations during the surgical procedures, as explained in more detail below.

As shown best in FIG. 3, the body 20 is generally T-shaped or Y-shaped having a longitudinal portion 22 extending along the longitudinal axis LA1, and crosswise portion 24 extending crosswise of the longitudinal portion generally along a crosswise axis CA of the body. The crosswise portion 24, which is at a distal end of the longitudinal portion 22, has a width W1 greater than the width W2 of the longitudinal portion so that in general the width of the body 12 tapers proximally. As explained in more detail below, actuators, locks, and couplers are coupled to the body 12.

Figure 7:
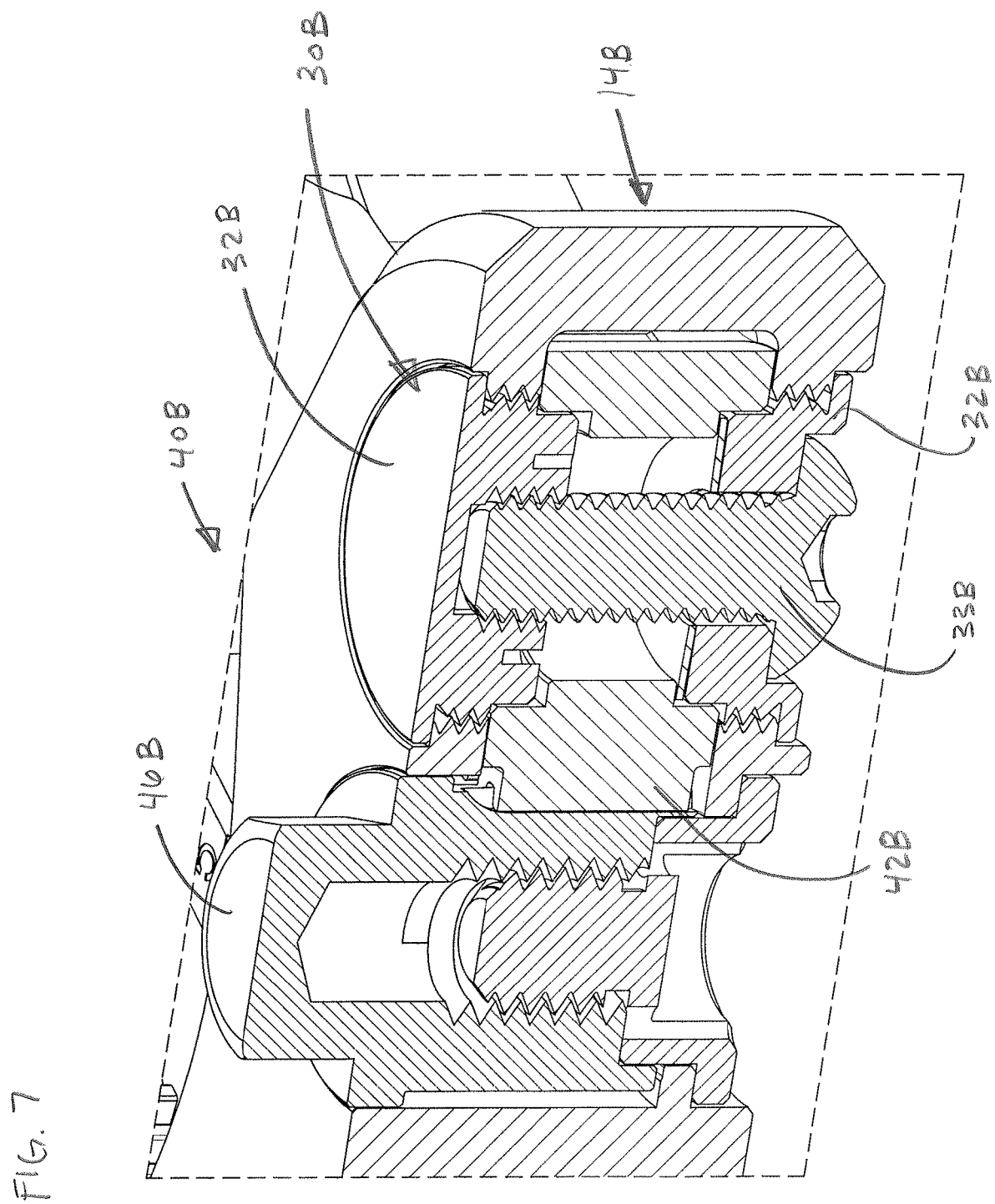
FIG. 7 is a cross-sectional perspective of a right arm and an associated pinion of the retractor.

Referring to FIGS. 4 and 5, each of the retracting arms 14A, 14B, 14C are independently operable to selectively move the arms relative to the body 12. The left and right retracting arms 14A, 14B are selectively rotatable in a horizontal plane about respective axes RA1, RA2 relative to the body 12, thereby allowing the left and right blades 16A, 16B to be movable away from and toward one another in a generally lateral direction relative to the longitudinal axis LA1 between fully closed and fully opened positions. Each of the left and right retracting arms 14A, 14B is rotatably coupled to the body 12 by left and right pins, generally indicated at 30A, 30B, respectively. The left pin 30A is coupled to a left side portion of the crosswise portion 24, and the right pin 30B is coupled to the right side portion of the crosswise portion. In the illustrated embodiment, each pin 30A, 30B includes upper and lower bearings 32A, 32B and a fastener 33A, 33B (e.g., a screw or bolt) fastening the bearings to one another. As shown in FIG. 7, the upper bearing 32A, 32B interfaces with an upper portion of the body 12 and the lower bearing interfaces with a lower portion of the body, thereby enabling rotation of the corresponding retracting arm 14A, 14B about the respective axes RA1, RA2. As explained in more detail below, each of the left and right retracting arms 14A, 14B is selectively rotatable about the corresponding pin 30A, 30B through two different mechanisms: a rack and pinion mechanism and a lever mechanism.

As seen best in FIGS. 6 and 7, each rack and pinion mechanisms includes a pinion, generally indicated at 40A, 40B, respectively, rotatably coupled to the body 12, and a rack (e.g., an arcuate rack) 42A, 42B, respectively, fixed to or apart of the corresponding retracting arm 14A, 14B. The pinions 40A, 40B include teeth meshing with teeth of the respective racks 42A, 42B. Each of the pinions 40A, 40B includes a tool coupler 46A configured to couple to a tool (not shown) for driving rotation of the pinion. The illustrated tool coupler 46A, 46B comprises a hexagonal head configured to receive a hexagonal socket of a wrench or other tool for driving rotation. In the illustrated embodiment, rotation of the left pinion 40A in a clockwise direction (as indicated by arrow A1) opens the left blade 16A by rotating the left retracting arm 14A to move the left blade generally in a left direction away from the longitudinal axis LA1, and rotation of the right pinion 40B in a counterclockwise direction (as indicated by arrow A2) opens the right blade 16b by rotating the right retracting arm 14B to move the right blade generally in a right direction away from the longitudinal axis. Each of the pinions 40A, 40B are independently operable to independently open and close the left and right blade 16A, 16B.

Figure 8:
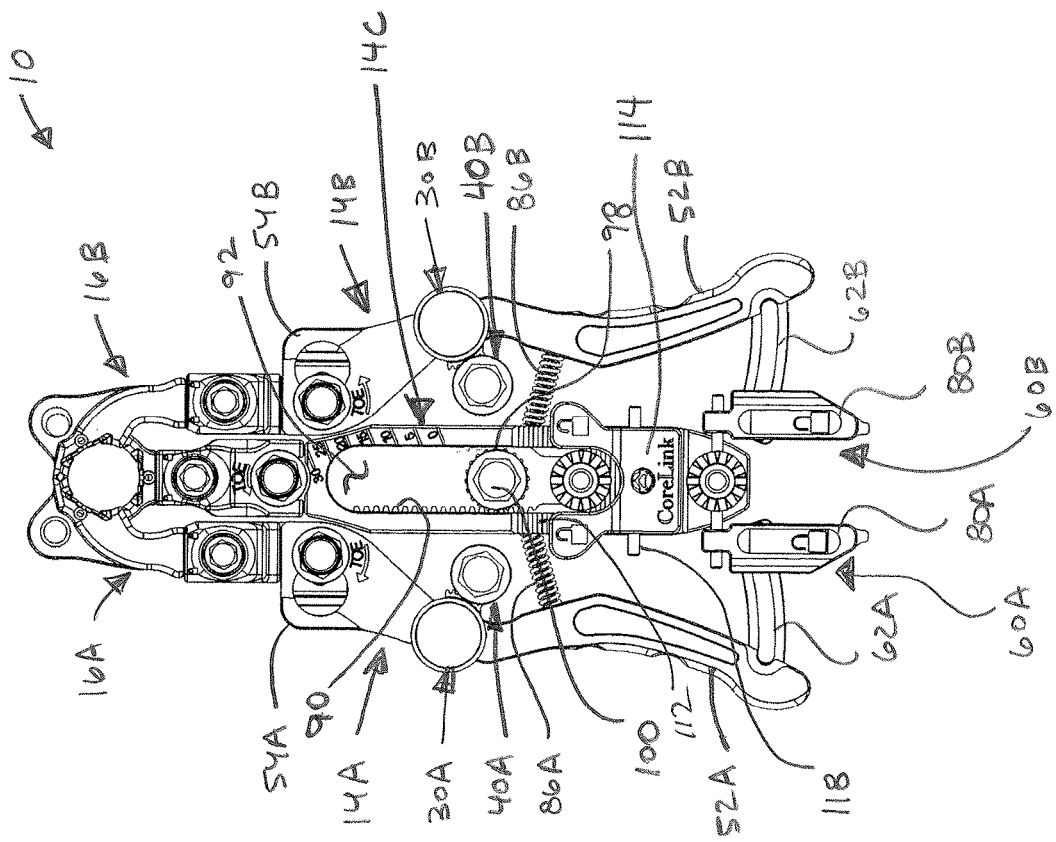
FIG. 8 is a top plan view similar to FIG. 3, but with a body of the retractor being removed from the retractor.

Referring to FIGS. 6 and 8, each lever mechanism includes an effort arm portion 52A, 52B, and a load arm portion 54A, 54B of the corresponding arm 14A, 14B. The effort arm portion 52A, 52B extends proximal of the corresponding pin 30A, 30B, and the load arm portion 54A, 54B extends distal of the corresponding pin. In use, as shown in FIGS. 4 and 5, generally lateral forces F1, F2 can be applied to one or both of the respective effort arm portions 54A, 54B of the left and right arms 14A, 14B to move the arm toward the longitudinal axis LA1. Movement of the effort arm portion 52A, 52B toward the longitudinal axis LA1 imparts movement of the corresponding load arm portion 54A, 54B away from the longitudinal axis. Thus, in one example the left and right effort arm portions 52A, 52B can be squeezed toward the longitudinal axis LA1 by a user's hand to manually open by hand the left and right blades 16A, 16B. Moving the left and right effort arm portions 52A, 52B toward the longitudinal axis LA reduces the crosswise footprint (e.g., width) extending crosswise between the left and right effort arm portions, while increasing the crosswise footprint (e.g., width) extending crosswise between the left and right load arm portions 54A, 54B. The left and right effort arm portions 52A, 52B may be configured to nest at least partially within the corresponding sides of the body 12 to further reduce the crosswise footprint therebetween. In the closed configuration (FIG. 3), the left and right effort arm portions 52A, 52B have a maximum crosswise footprint W3. This maximum crosswise footprint W3 may be less than or equal to the width W1 of the crosswise portion 24 of the body 12. In the open configuration (FIG. 5), the effort arm portions 54A, 54B have a maximum crosswise footprint W4. This maximum crosswise footprint W4 may be less than or equal to the width W1 of the crosswise portion 24 of the body 12.

Figure 9:
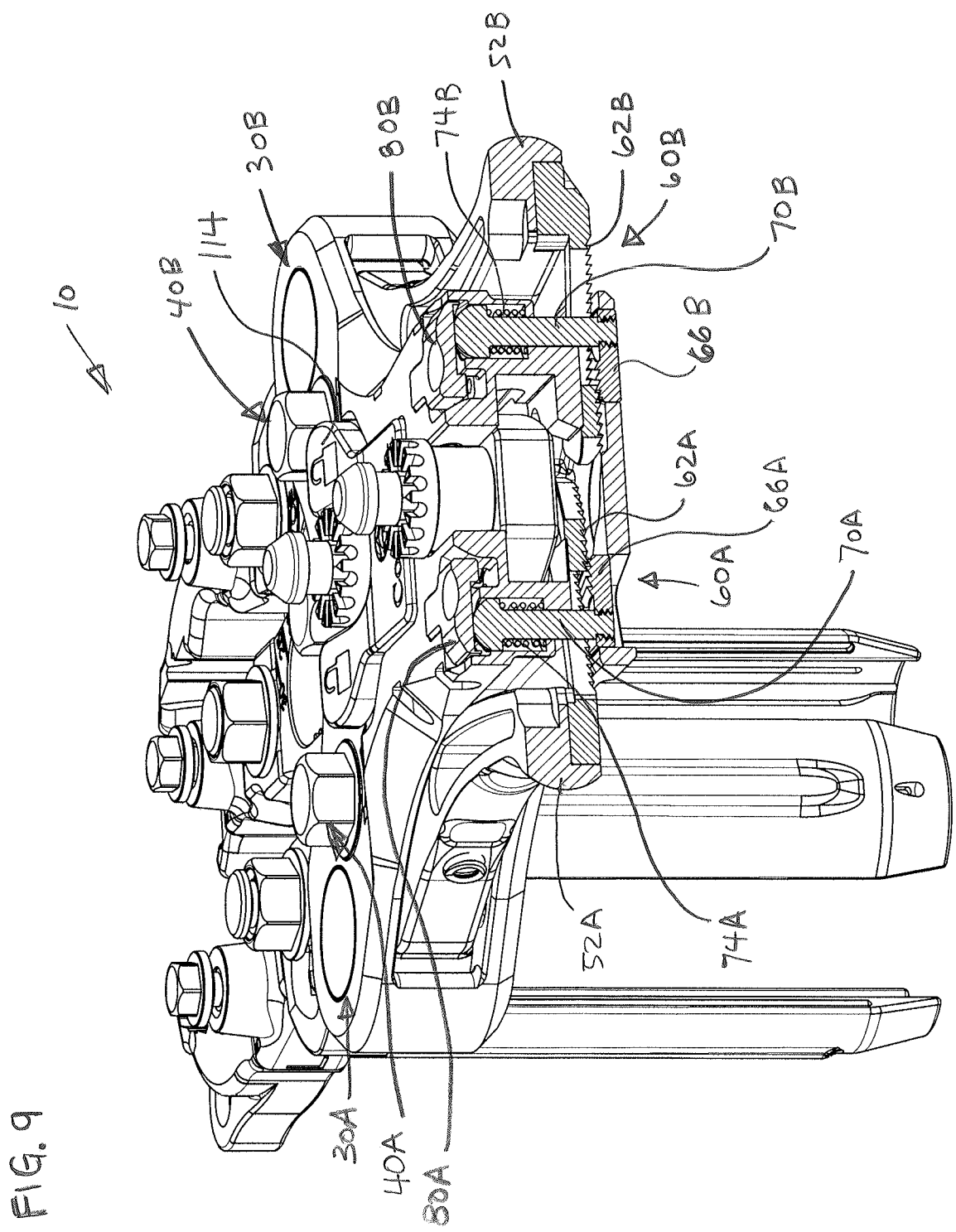
FIG. 9 is a cross-sectional perspective of the retractor showing cross sections of ratchet mechanisms.
Figure 10:
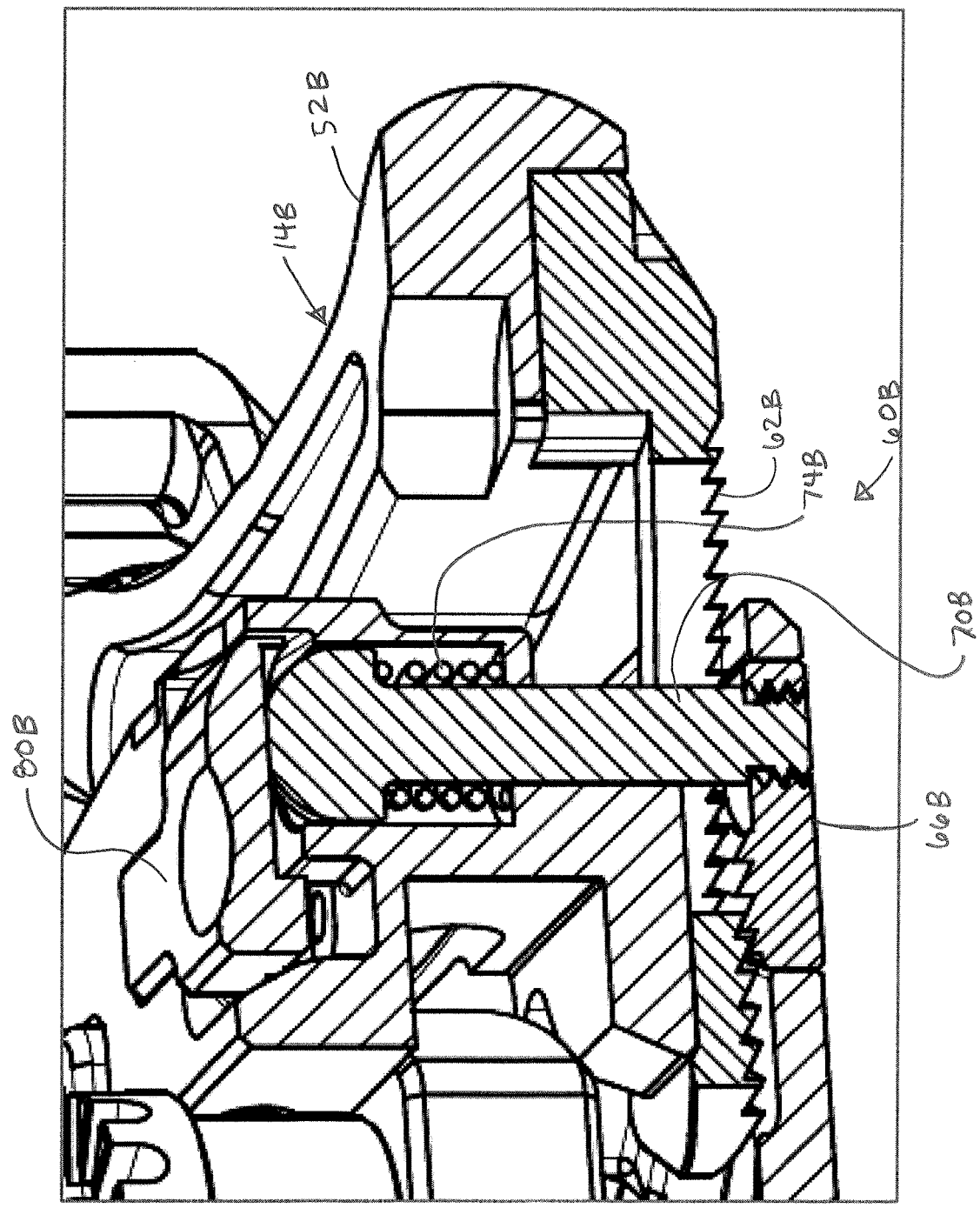
FIG. 10 is an enlarged detail of FIG. 9.
Figure 11:
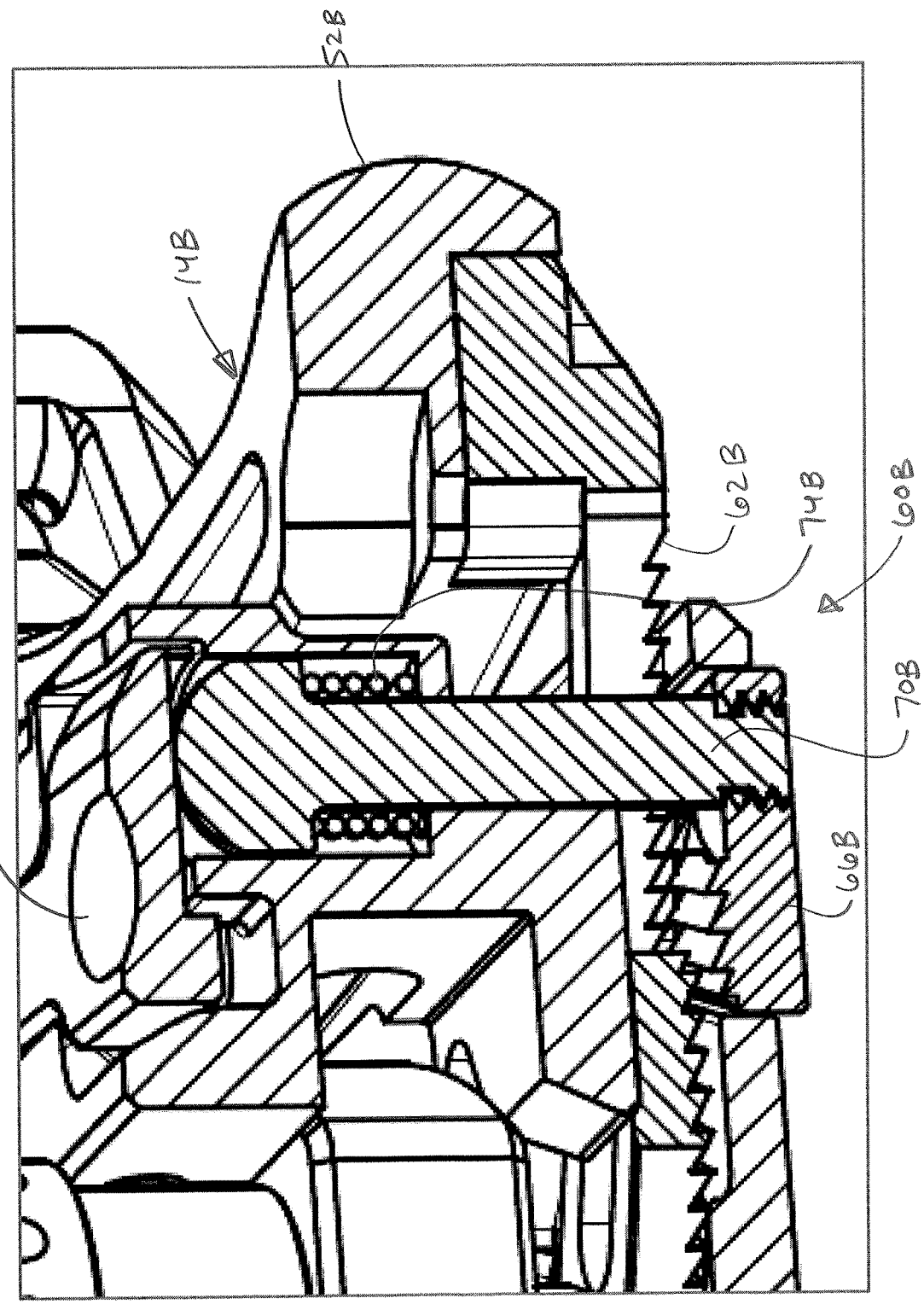
FIG. 11 is similar to FIG. 10 showing the ratchet mechanism in a released configuration.

Each of the left and right retracting arms 14A, 14b has an anti-backoff mechanism associated therewith for independently inhibiting the left and right retracting arms from backing off its selective rotational position relative to the body 12. Referring to FIGS. 9-11, each anti-back off mechanism includes a ratchet mechanism, generally indicated at 60A, 60B, respectively. Each ratchet mechanism 60A, 60B respectively includes a ratchet rack 62A, 62B (e.g., a toothed rack) coupled to the corresponding one of the left and right retracting arms 14A, 14B and extending toward the longitudinal axis LA1, and a pawl 66A, 66B configured to engage (e.g., mesh) with the ratchet rack as the effort arm portion 52A, 52B is moved inward toward the longitudinal axis. Each pawl 66A, 66B is biased into meshing engagement with the ratchet rack 62A, 62B. A post 70A, 70B couples the pawl 66A, 66B to the body 12, and a spring 74A, 74B applying a biasing force on the post to bias the pawl toward the ratchet rack into meshing engagement therewith. Each ratchet mechanism 60A, 60B is configured to inhibit movement of the corresponding effort arm portions 52A, 52B laterally away from the longitudinal axis LA. Each ratchet mechanism 60A, 60B is further configured to be selectively released by disengaging the pawl 66A, 66B from the ratchet rack 62A, 62B. In the illustrated embodiment, each ratchet mechanism 60A, 60B includes a ratchet actuator 80A, 80B (e.g., a rotatable paddle or button) operable to move the post 70A, 70B against the biasing force of the spring 74A, 74B and move the pawl 66A, 66B away from the ratchet rack 62A, 62B. Referring to FIG. 8, closing springs 86A, 86B (e.g., compression springs) bias the respective left and right retracting arms 14A, 14B in the closed positions, such that the corresponding arm moves to the closed position under the force of the corresponding spring upon selective release of the pawl 66A, 66B from the ratchet rack 62A, 62B.

Figure 12:
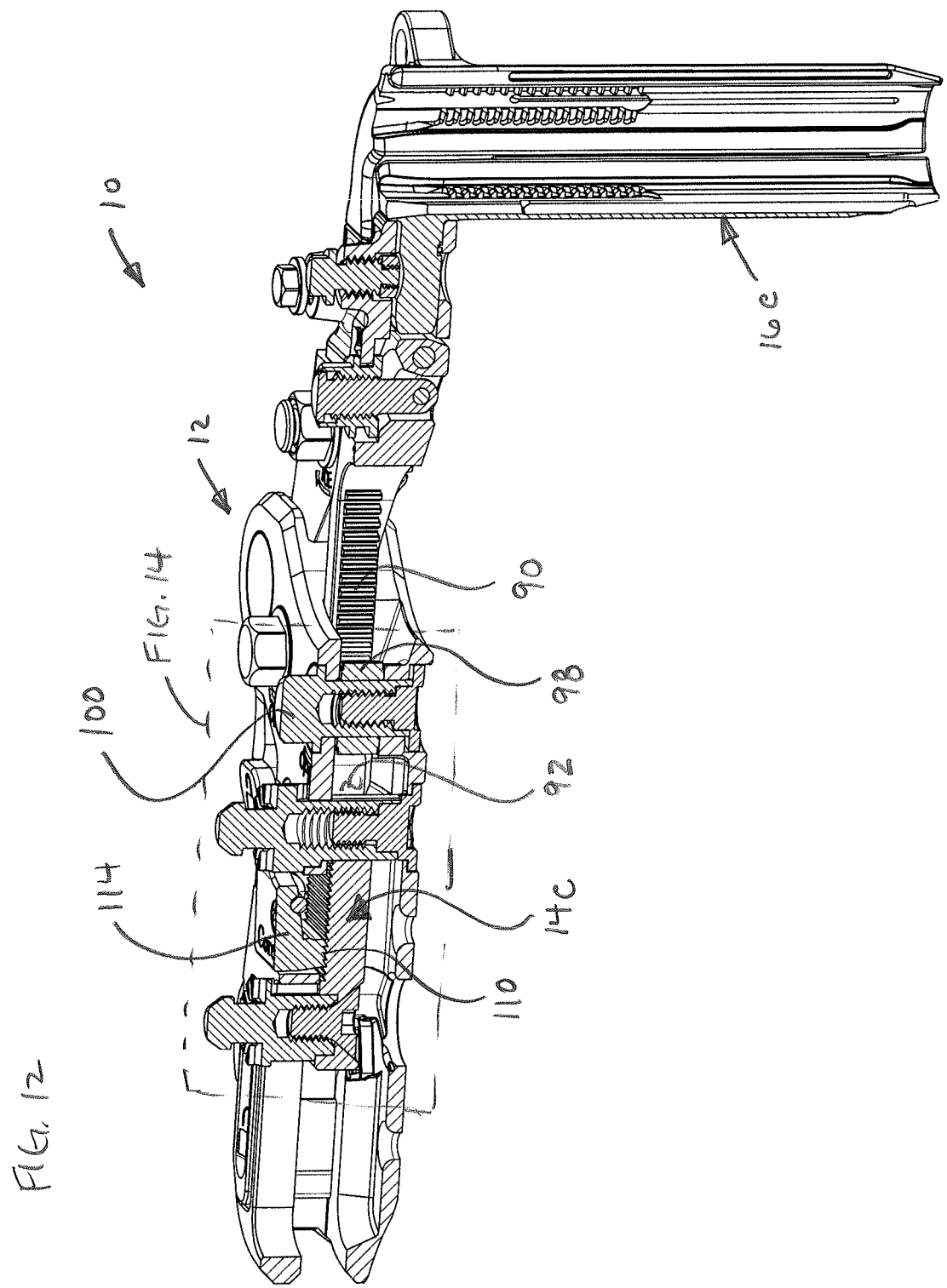
FIG. 12 is a cross-sectional perspective of the retractor in the closed, non-toed position.
Figure 13:
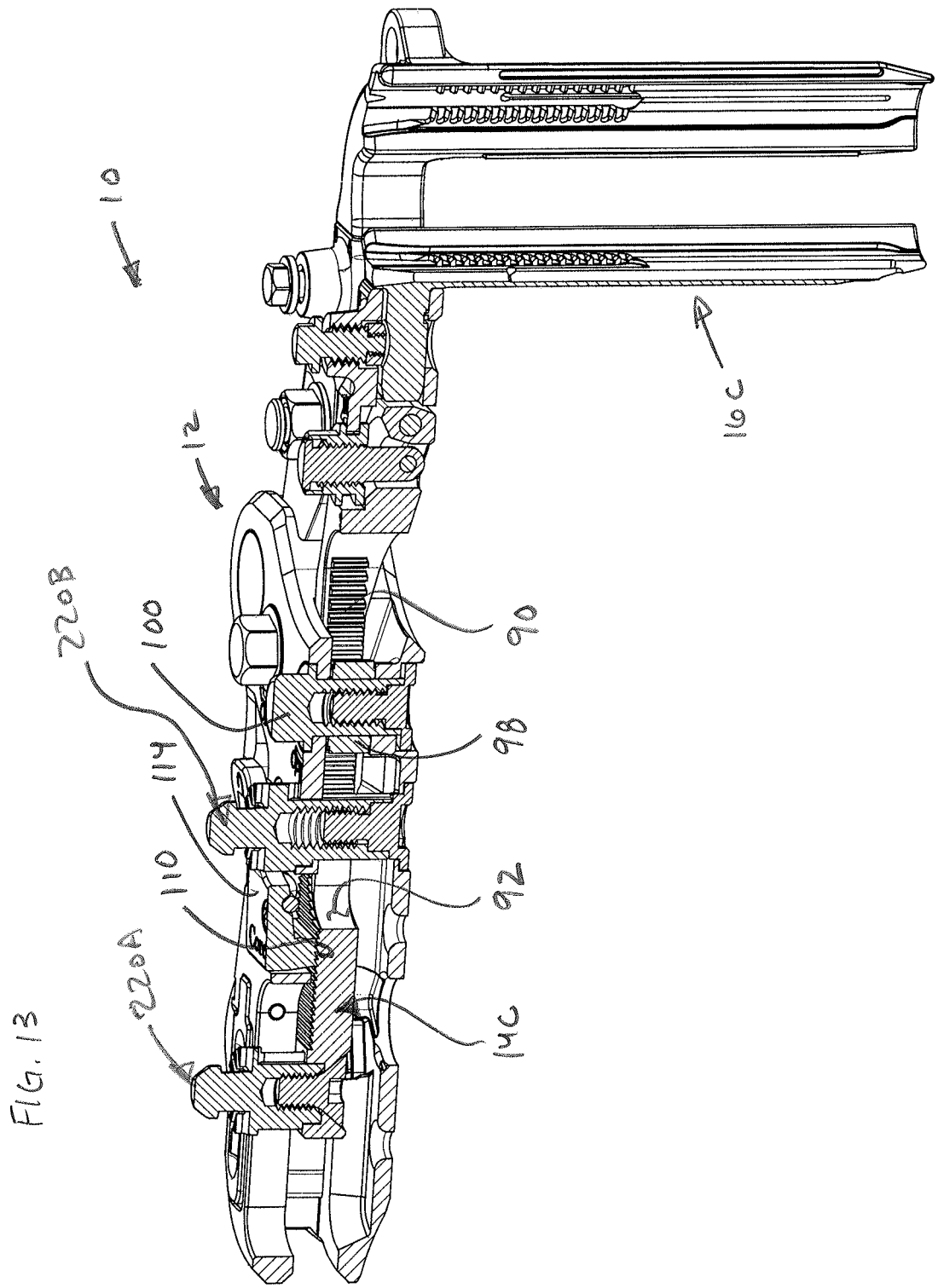
FIG. 13 is similar to FIG. 12 with a center arm of the retractor in the open, non-toed position.
Figure 14:
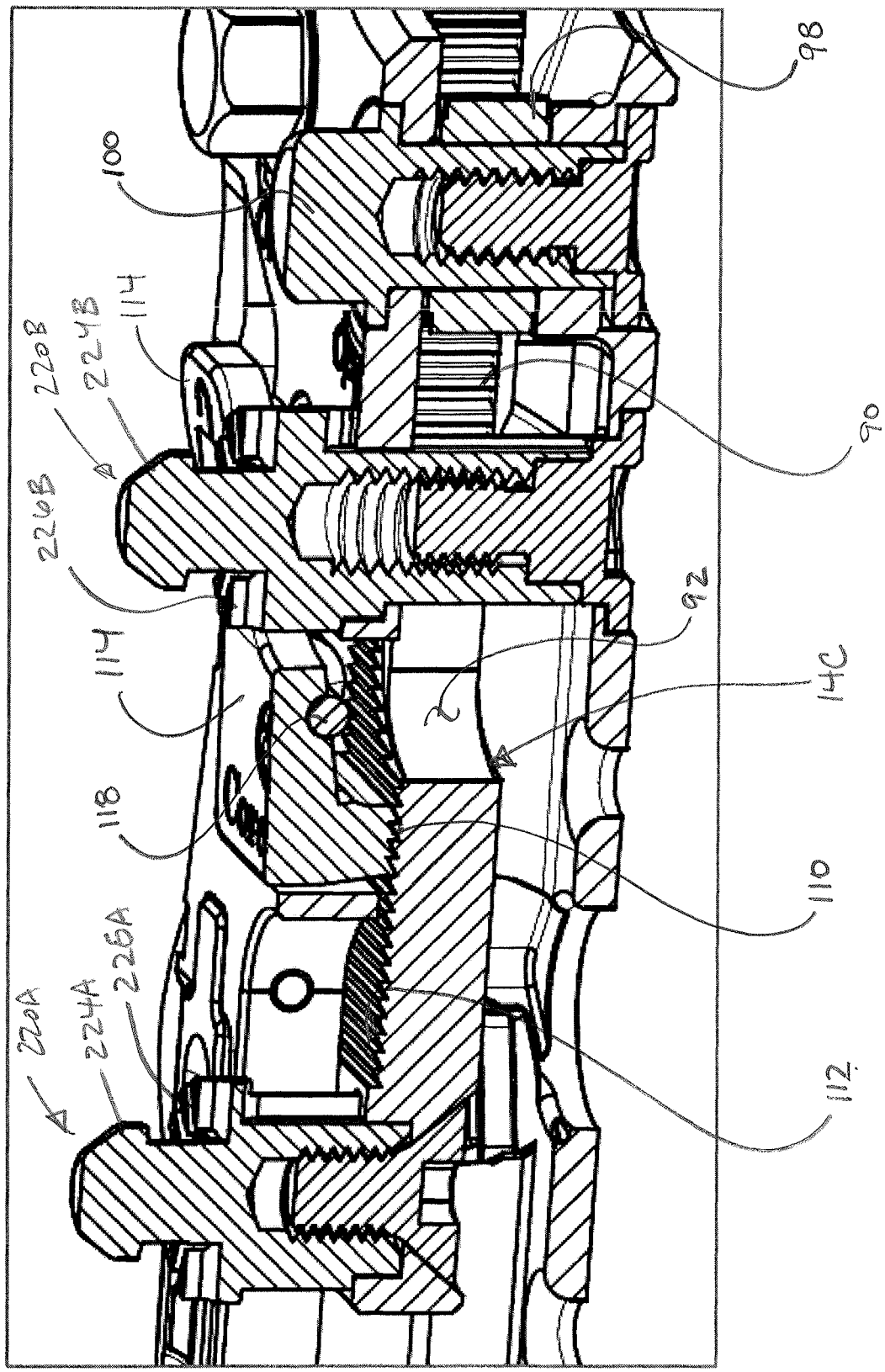
FIG. 14 is an enlarged, detail view of FIG. 13.

Referring to FIGS. 12-14, the center arm 14C is movable linearly generally along the longitudinal axis LA between fully a closed position (FIGS. 12 and 13) and a fully opened position (FIG. 14). In the illustrated embodiment, a rack and pinion mechanism enables movement of the center arm 14C relative to the body 12. The rack and pinion mechanism includes a toothed, linear rack 90 on the center retracting arm 14C, such as within a slot 92 defined by the center arm, and a pinion 98 rotatably coupled to the body 12 and meshing with the linear rack. The pinion 98 includes a pinion actuator or tool coupler 100 configured to couple to a tool (not shown) for driving rotation of the pinion. The illustrated tool coupler 100 comprises a hexagonal head configured to receive a hexagonal socket of a wrench or other tool for driving rotation. In the illustrated embodiment, rotation of the pinion 98 in a counterclockwise direction (as indicated by arrow A3 in FIG. 3) moves the center retracting arm 14C and the center blade 16C generally in a proximal direction.

Referring still to FIGS. 12-14, an anti-backoff mechanism inhibits unintentional movement of the center retracting arm 14C in a distal direction, thereby inhibiting incidental movement of the center retracting arm toward its closed position. The illustrated anti-backoff mechanism includes a detent 110 (e.g., a tooth member) configured to mesh with upper teeth 112 (e.g., an upper rack) on an upper surface of the center retracting arm. The detent 110 is biased to mesh with the upper teeth 112 by a spring (not shown) or other biasing element. A detent actuator 114 is coupled to the detent 110 and is hingedly coupled to the body 12 by one or more pins 118. The detent actuator 114 may comprise a paddle or button that rotates about the one or more pins 118 to selectively release the detent 110 from the upper teeth 112.

As can be seen from the drawings, each of the unlock or release actuators 80A, 80B, 114 (e.g., paddles or buttons) are accessible by the user at an upper surface of the body 12. Thus, the user may selectively release or unlock anyone of the arms 16A, 16B, 16C by having access to the upper surface of the body 12, and not requiring access to any sides or the bottom of the body. Moreover, the pinion actuators 46A, 46B, 100 for each of the pinions of the rack and pinion mechanisms are accessible at the upper surface of the body 12. In addition, the construction of the body 12 and the left and right arms 14A, 14B gives the retractor 10 a low profile and provides sufficient leverage when squeezing the arms to move the left and right blades 16A, 16B to the open positions.

Referring to FIGS. 17-20, each of the blades 16A, 16B, 16C includes an arcuate blade body 116A, 116B, 116C, and a tongue 120A, 120B, 120C (i.e., a male coupling) extending proximally from the blade body. The tongue 120A, 120B, 120C is removably couplable to a lug connector, generally indicated at 124A, 124B, 124C, which in turn is coupled to the corresponding one of the retracting arms 14A, 14B, 14C. In the illustrated embodiment, each lug connector 124A, 124B, 124C, is coupled to the corresponding arm by a corresponding toeing mechanism, generally indicated at 130A, 130B, 130C, which is generally known in the art. Thus, the toeing mechanism 130A, 130B, 130C allows canting of the lug connector 124A, 124B, 124C, which in turn, toes the corresponding blade body 116A, 116B, 116C. The construction of the toeing mechanisms 130A, 130B, 130C may be similar to those known in the art, including an actuator 134A, 134B, 134C with a hexagonal head for coupling with a tool. The blade body 116A, 116B, 116C may have a selected longitudinal length and may have a selected cross-sectional arcuate length, as is generally known in the art.

Figure 18:
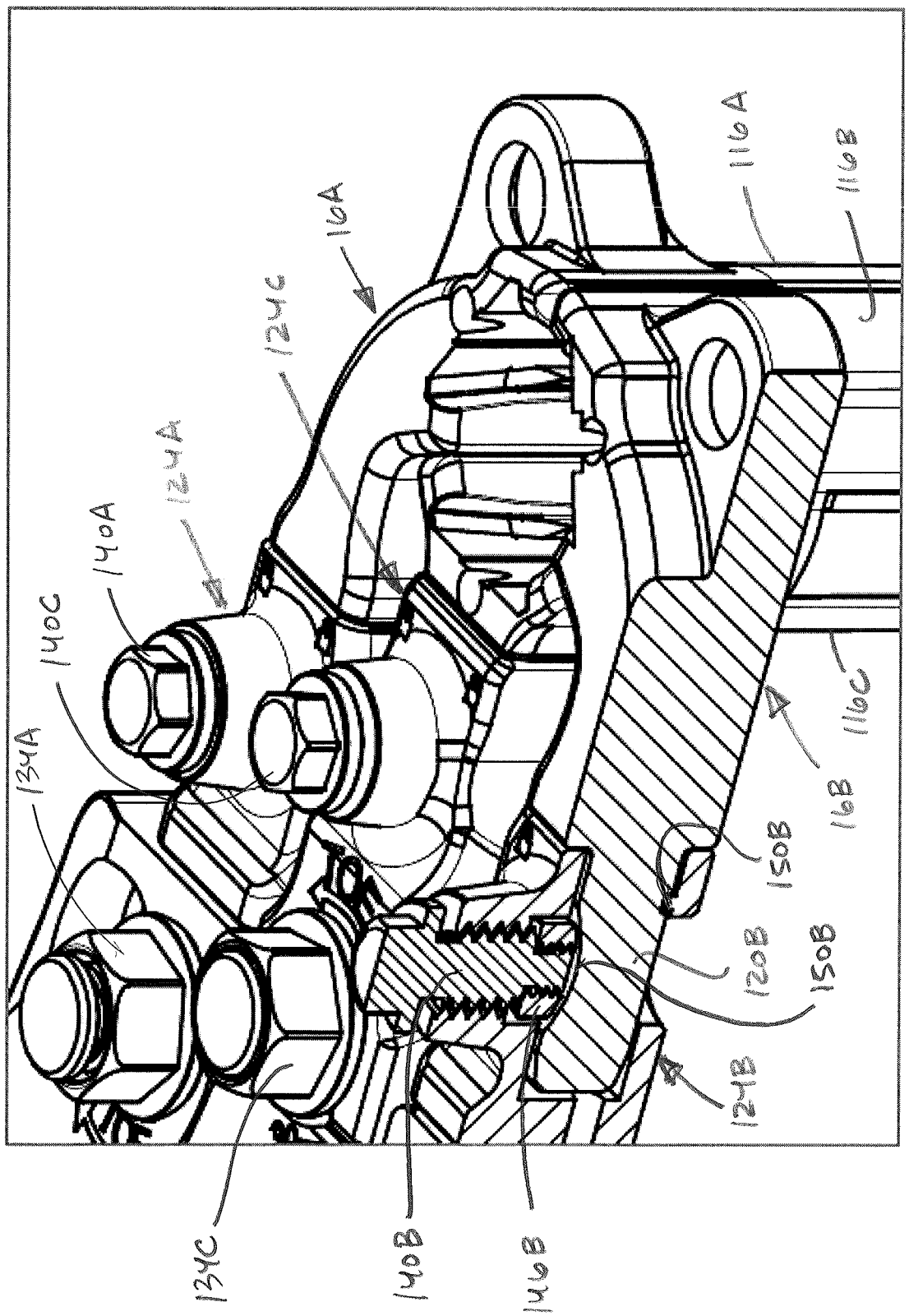
FIG. 18 is an enlarged, detail view of FIG. 17.
Figure 19:
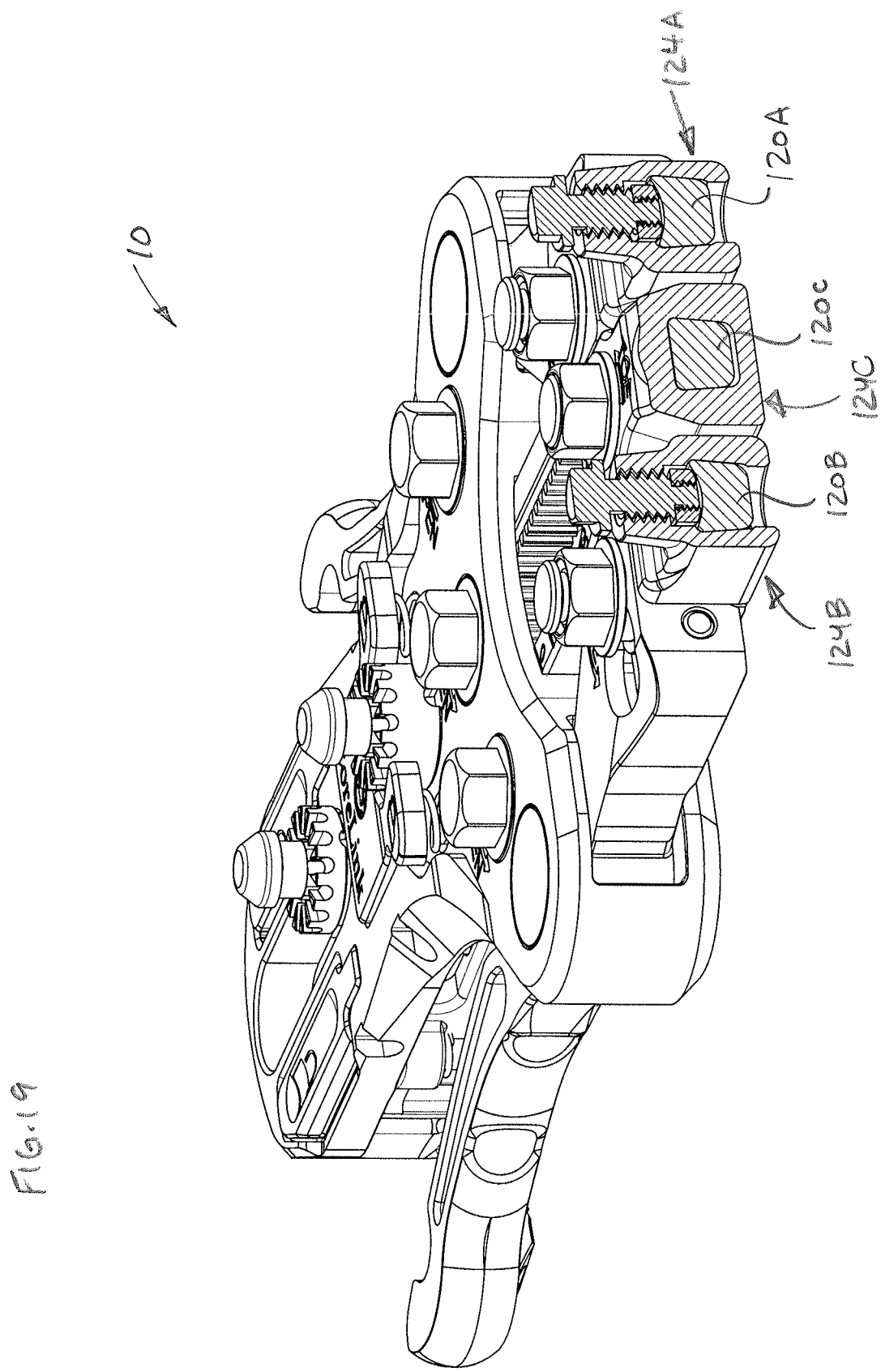
FIG. 19 is a cross-sectional perspective of the retractor with sections taken through lug portions of the arms.
Figure 20:
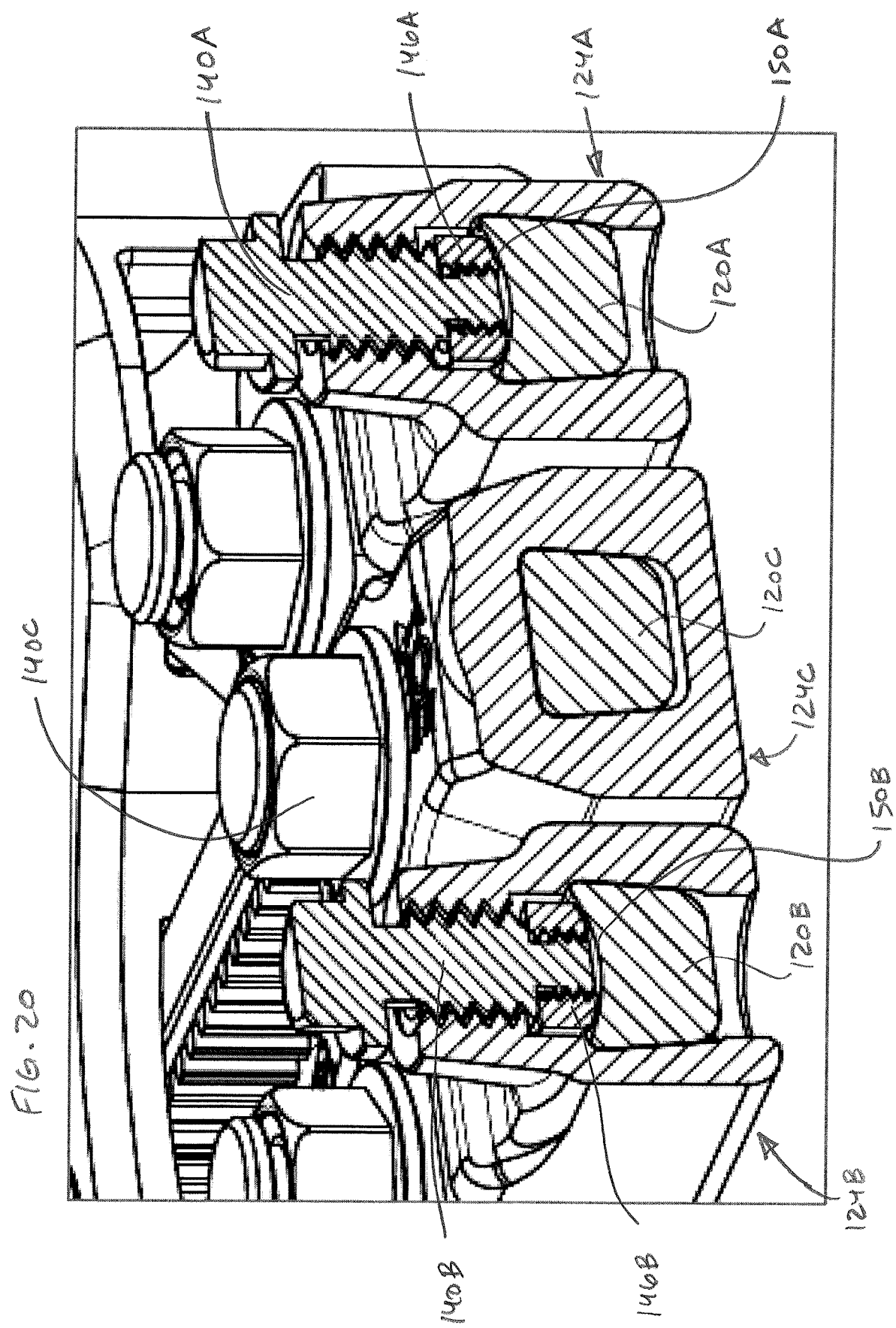
FIG. 20 is an enlarged, detail view of FIG. 19.

Referring to FIGS. 19 and 20, the illustrated tongue 120A, 120B, 120C of each blade 16A, 16B, 16C tapers from an upper surface toward a lower surface thereof such that the width of the tongue at an upper portion is greater than a width of the tongue at a lower portion, giving the tongue a generally trapezoidal cross-sectional shape. The lug connector 124A, 124B, 124C of each arm 16A, 16B, 16C has a body defining a socket (i.e., a female coupling) having a cross-sectional shape corresponding generally with the cross-sectional shape of the tongue 120A, 120B, 120C and configured to receive the tongue therein, as explained in more detail below. A set screw 140A, 140B, 140C threadably coupled to the lug connector body engages the tongue 120A, 120B, 120C within the socket to secure the tongue within the socket and inhibit the tongue from unintentionally withdrawing from and moving within the socket. The set screw 140A, 140B, 140C may include a hexagonal head or other head for coupling to a tool, such as a wrench or other driver. The set screw 140A, 140B, 140C includes a knob 146A, 146B, 146C (or a convex tip) at the end of its shaft that is sized and shaped to be received in a recess or pocket 150A, 150B (pocket of the middle tongue is hidden) defined by an upper surface of the tongue 120A, 120B, 120C. In addition, as shown in FIG. 18, a locking rib 152B (the other locking ribs are hidden) within each socket is receivable within a groove defined by and extending cross-wise of the tongue 120A, 120B, 120C to further inhibit the tongue 120A, 120B, 120C from unintentionally withdrawing from and moving within the socket.

The cross-sectional size of the socket is such that the tongue 120A, 120B, 120C is insertable into the socket in an upper position relative to the socket so that the tongue clears the locking rib 152B as it is inserted into the socket. With the tongue 120A, 120B, 120C fully inserted in the socket, the set screw 140A, 140B, 140C is tightened to force the tongue downward into a lower position within the socket. The cross-sectional dimension of the socket narrows at the lower portion of the socket to create friction fit between the tongue 120A, 120B, 120C and the socket. The set screw 140A, 140B, 140C may be tightened until the tongue 120A, 120B, 120C bottoms out at the bottom wall of the socket and the rib 152B (other the other ribs not shown) is received in the groove. The combination of the set screw 140A, 140B, 140C, the pocket 150B, the friction fit, and the rib-in-groove 150B inhibits movement of the blade relative to the arm, thereby reducing wobbling of the blade relative to the arm.

Figure 21:
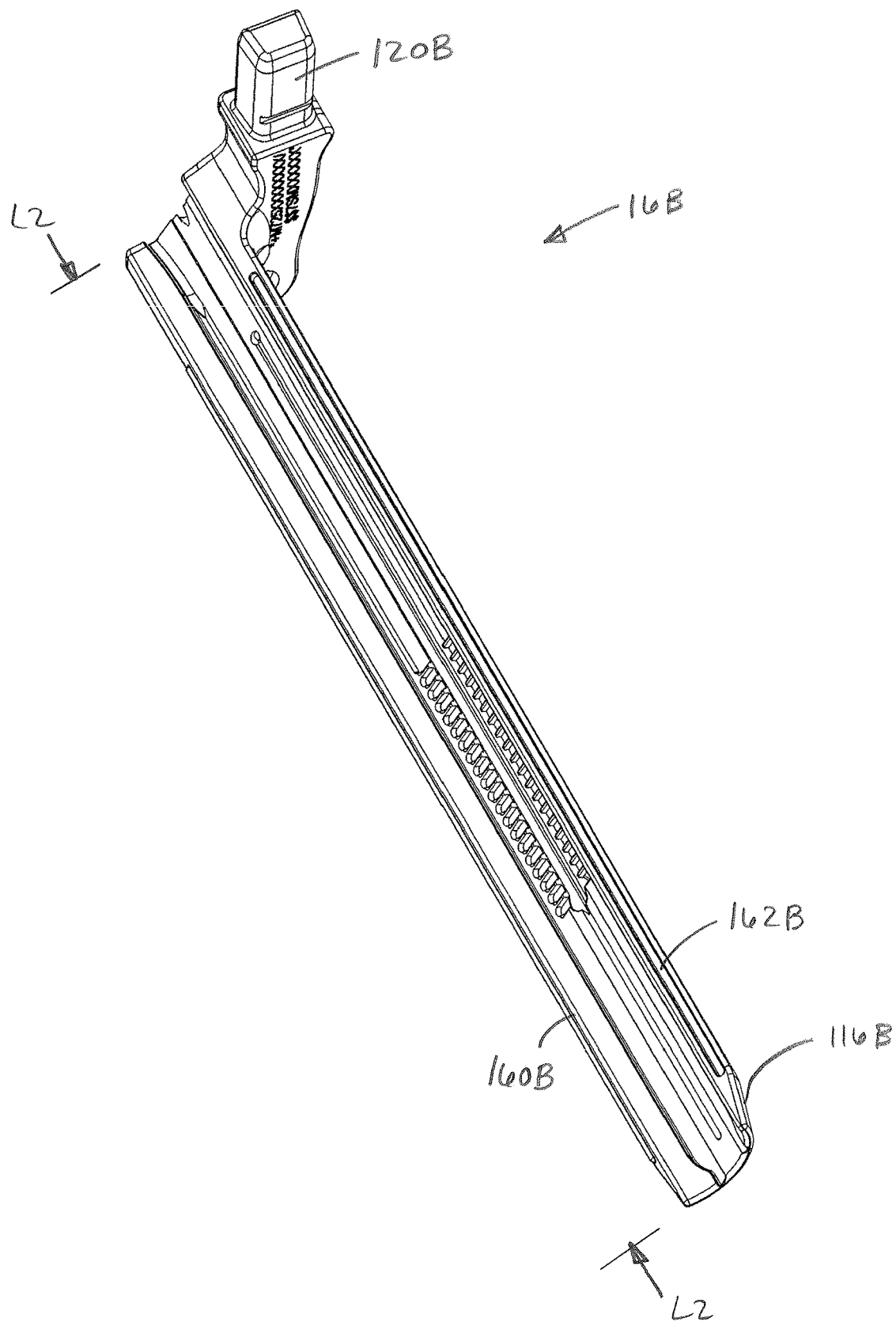
FIG. 21 is a perspective of a right blade of the retractor.
Figure 22:
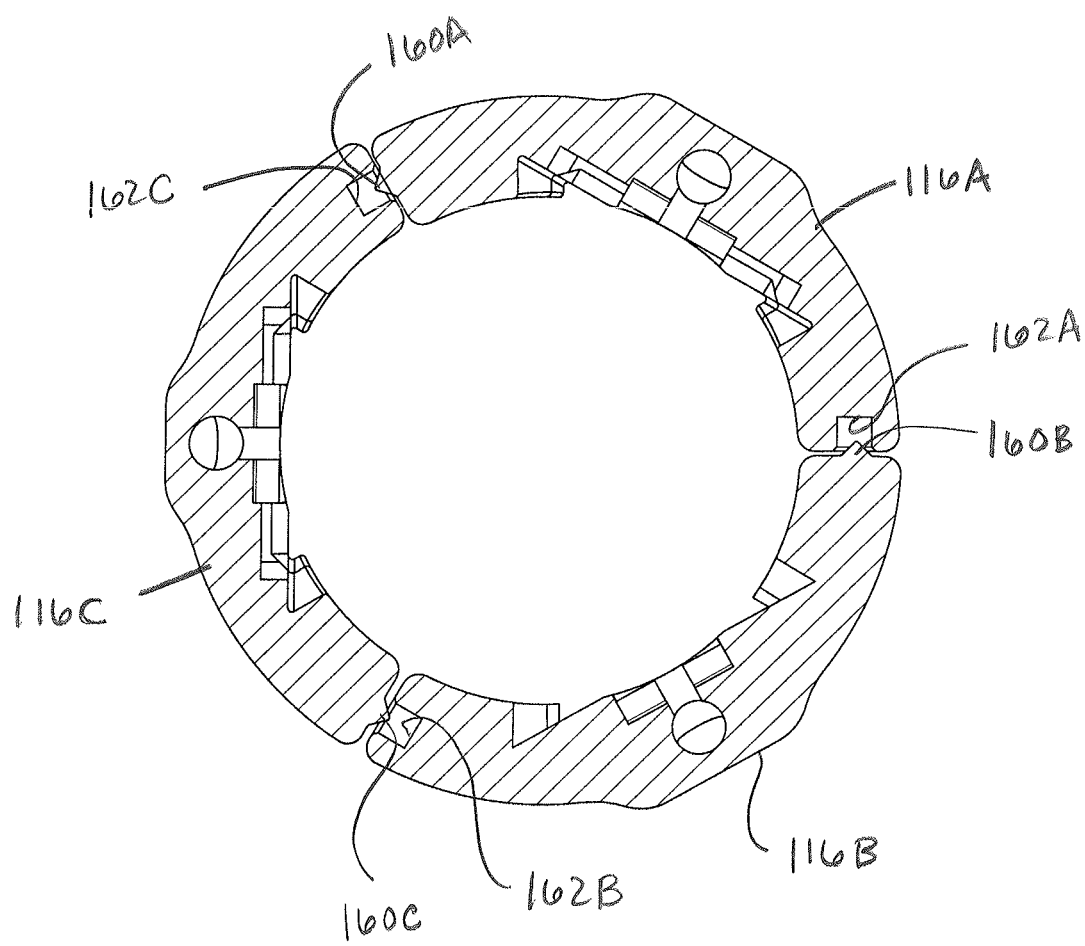
FIG. 22 is a cross section taken through line 22-22 in FIG. 15.

Referring to FIGS. 21 and 22, each blade body 116A, 116B, 116C includes a longitudinal rib 160A, 160B, 160C extending longitudinally on one arcuate side thereof, and a groove 162A, 162B, 162C extending longitudinally on the other, opposite arcuate side. The longitudinal rib 160A, 160B, 160C is configured to mate with a corresponding groove 162A, 162B, 162C of one adjacent blade body 116A, 116B, 116C, and the groove is configured to mate with a corresponding longitudinal rib of the other adjacent blade body. When the blades 16A, 16B, 16C are in the fully closed configuration, the blade bodies 116A, 116B, 116C are mated together to define a substantially closed circumference, as shown in FIG. 22 for example. In the illustrated embodiment, the longitudinal rib 160A, 160B, 160C extends continuously, as a single rib, along at least a majority of the length L2 of the corresponding arcuate side of the blade body 116A, 116B, 116C. The groove 162A, 162B, 162C also extends continuously, as a single groove, along at least a majority of the length of the corresponding arcuate side of the blade body 116A, 116B, 116C. In other embodiments, the groove 116A, 116B, 116C and/or the longitudinal rib 160A, 160B, 160C may not be continuous. Each of the groove 116A, 116B, 116C and longitudinal rib 160A, 160B, 160C may extend at least 50%, or at least about 60%, or at least about 70%, or at least about 75%, or at least about 80%, or at least about 90%, or at least about 95% of the length L2 of the blade body 116A, 116B, 116C.

Figure 23:
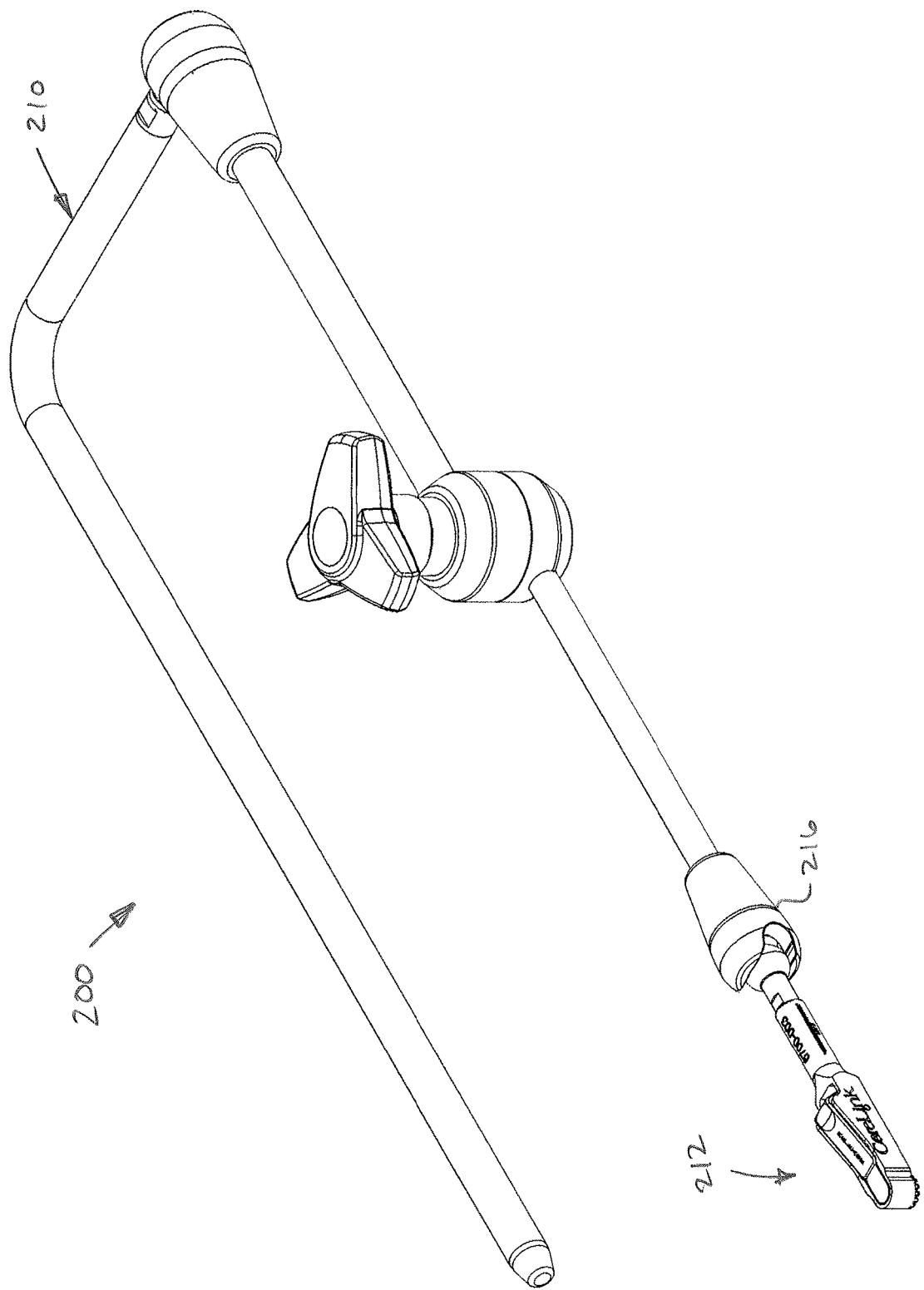
FIG. 23 is a perspective of an arm mount for a retractor.

Referring to FIG. 23, an arm mount for the retractor 10, or another retractor, is indicated generally at reference numeral 200. The arm mount 200 is configured to mount the retractor 10 on an operating table or bed or the like to free the hands of the user and assistants. The arm mount includes an arm, generally indicated at 210, and a retractor adaptor, generally indicated at 212, coupled to the arm. The arm 210 may be a conventional arm as is generally known in the art or another type of arm. A coupler 216 of the arm 210 couples the retractor adaptor 212 to the arm and allows articulation of the retractor adaptor 212 relative to the arm, and therefore, articulation of the retractor 10 relative to the arm.

Figure 15:
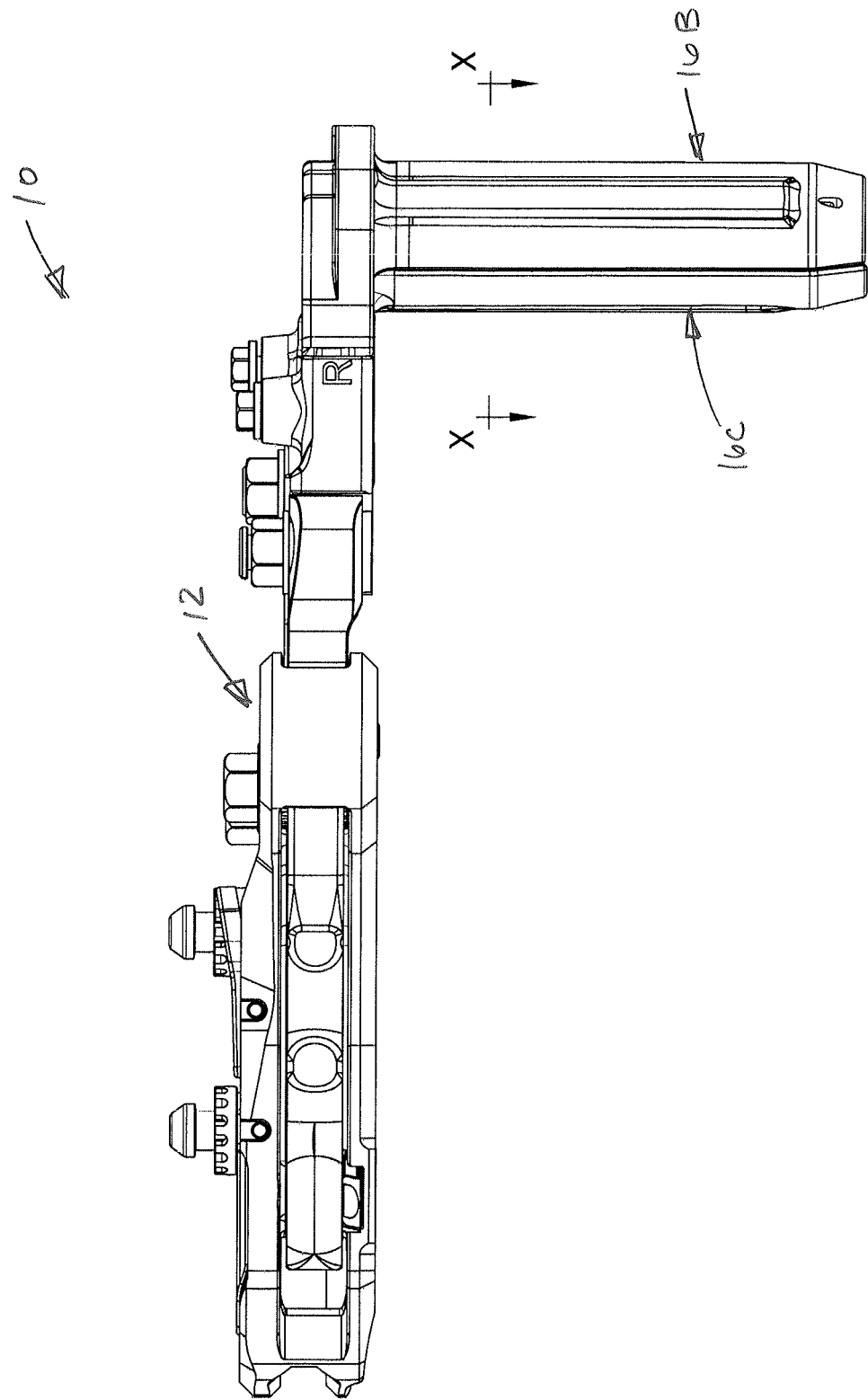
FIG. 15 is a side elevation of the retractor.
Figure 16:
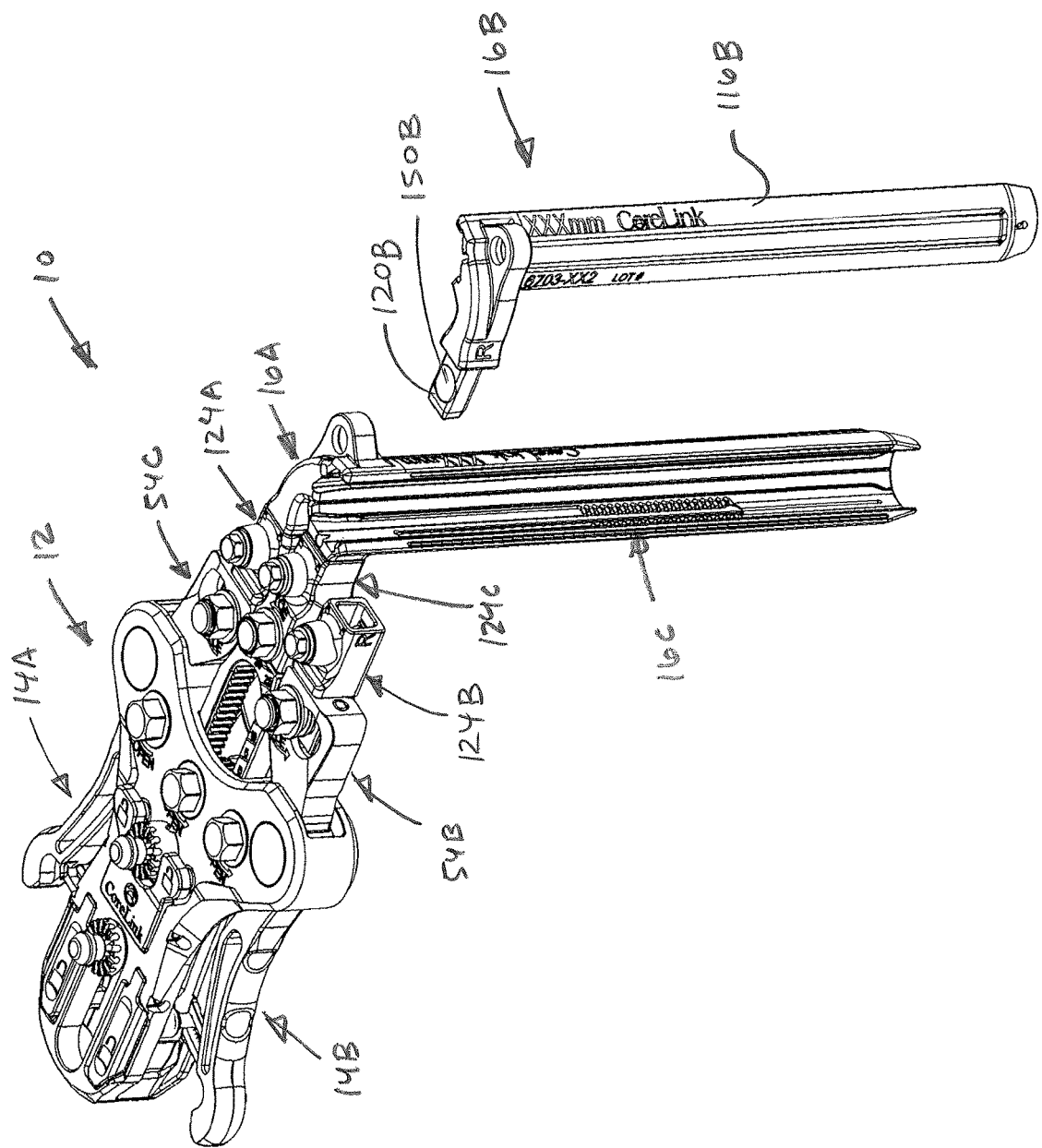
FIG. 16 a perspective of the retractor with a right blade exploded therefrom.
Figure 17:
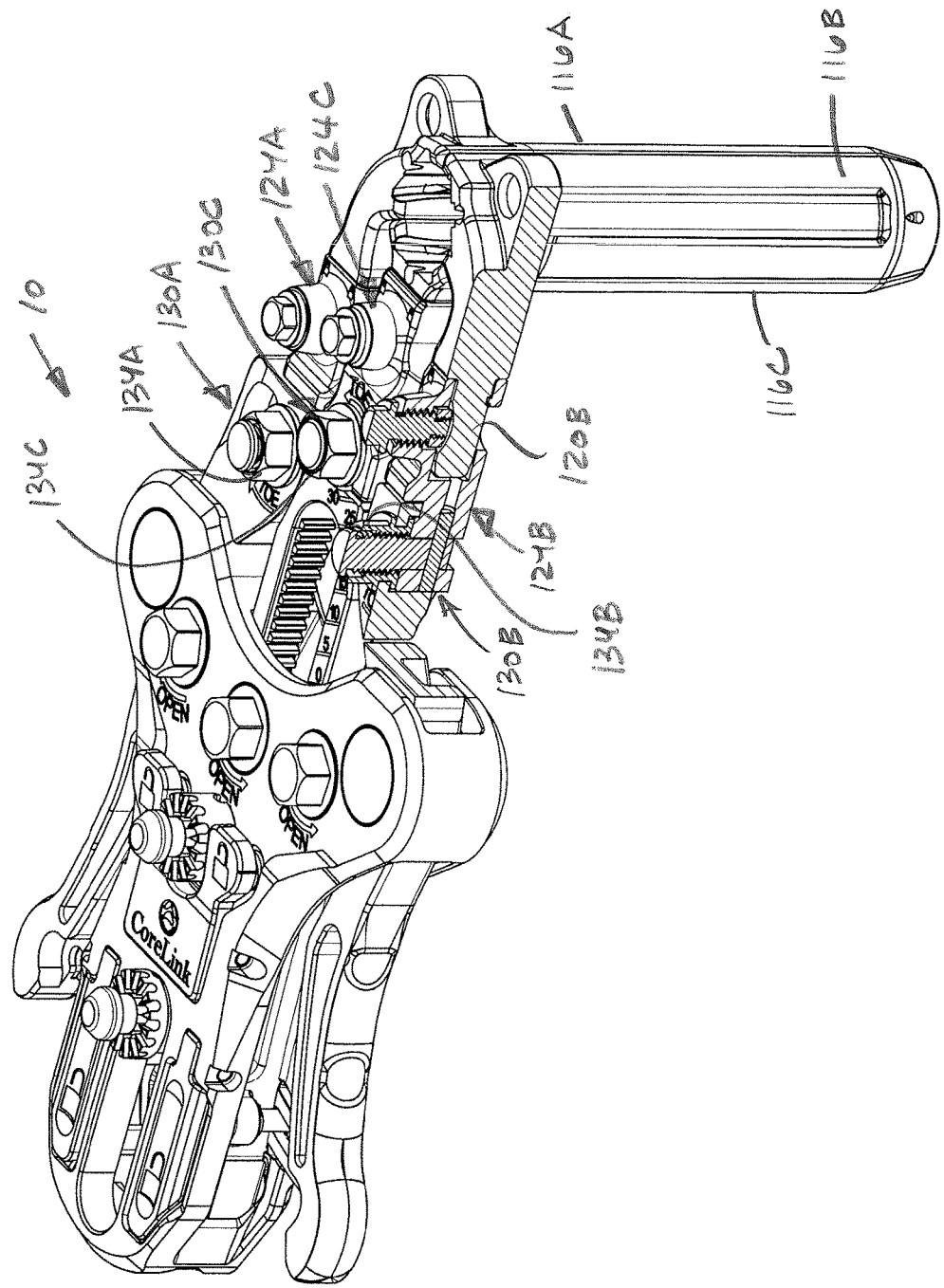
FIG. 17 is a cross-sectional perspective of the retractor with a distal end portion of the right arm in cross section.

The retractor adaptor 212 is couplable to the retractor 10 via an adaptor mount. The illustrated retractor 10 includes two adaptors mounts: a proximal adaptor mount 220A and a distal adaptor mount 220B, each indicated generally. The proximal adaptor mount 220A is coupled to and moves with the central arm 16C, and the distal adaptor mounts 220B is coupled to the body 12 and does not move with the central arm. Other than these differences, the adaptor mounts 220A, 220B are generally identical. As seen best in FIGS. 14 and 15, each adaptor mounts 220A, 220B includes a stud 224A, 224B including an enlarged button head, and annular row of teeth 226A, 226B surrounding the stud.

Figure 24:
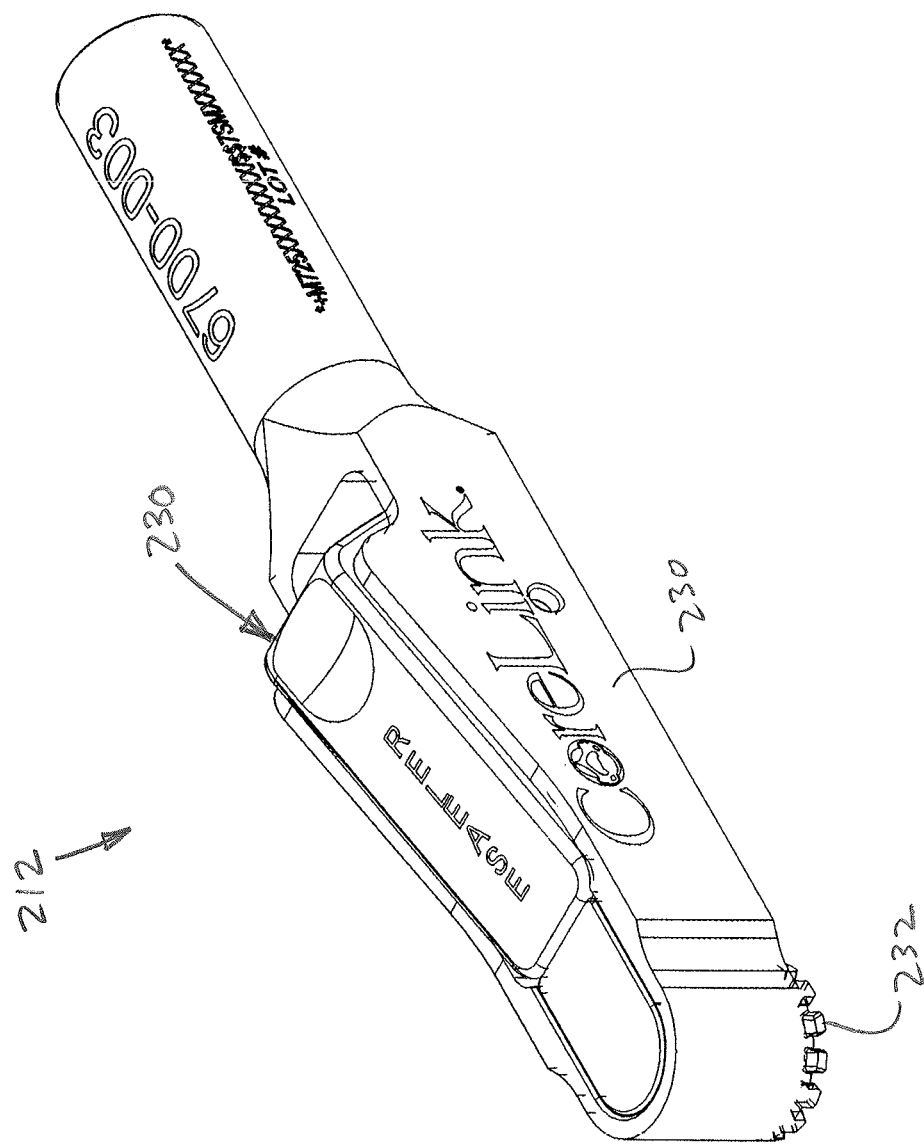
FIG. 24 is a perspective of an actuator adaptor of the arm mount.
Figure 25:
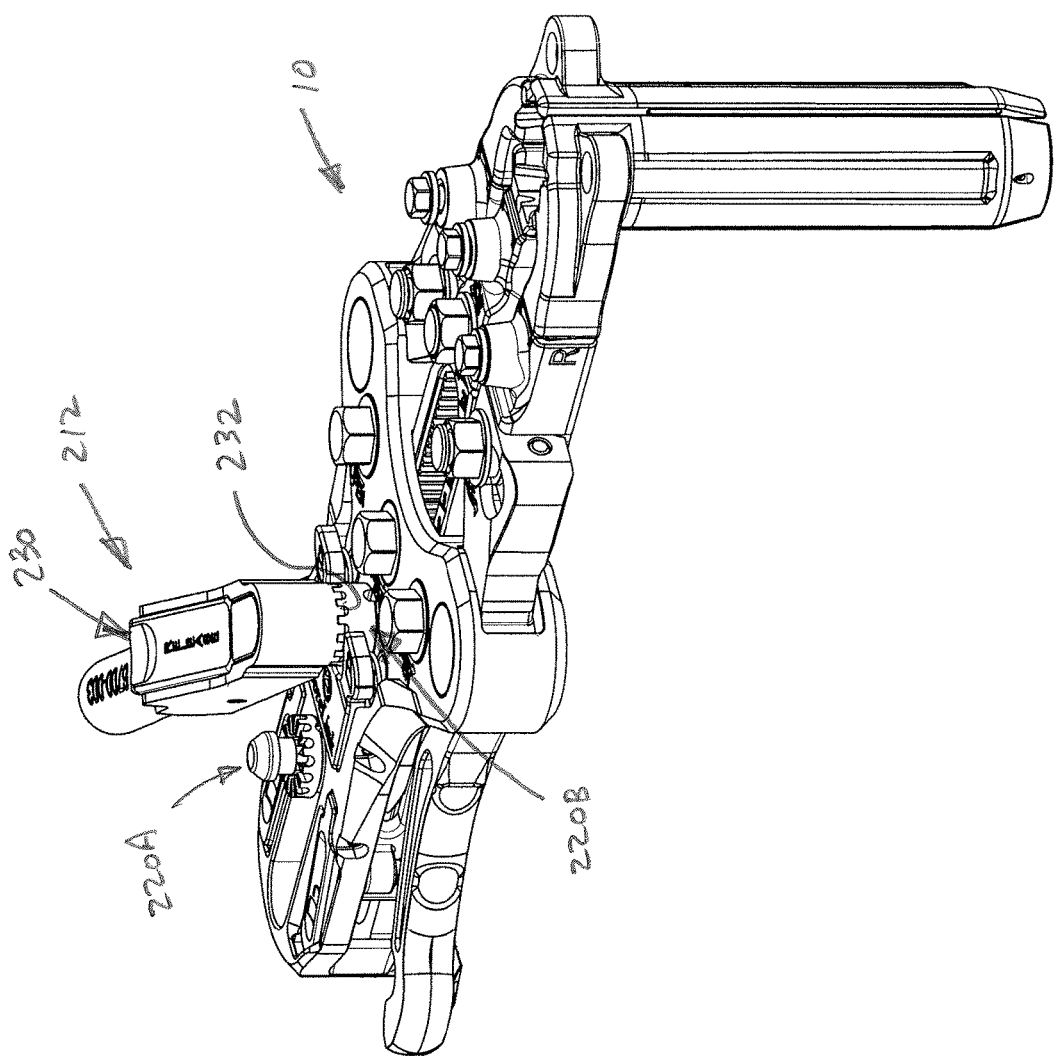
FIG. 25 is a perspective of the retractor and the actuator adaptor coupled thereto.
Figure 26:
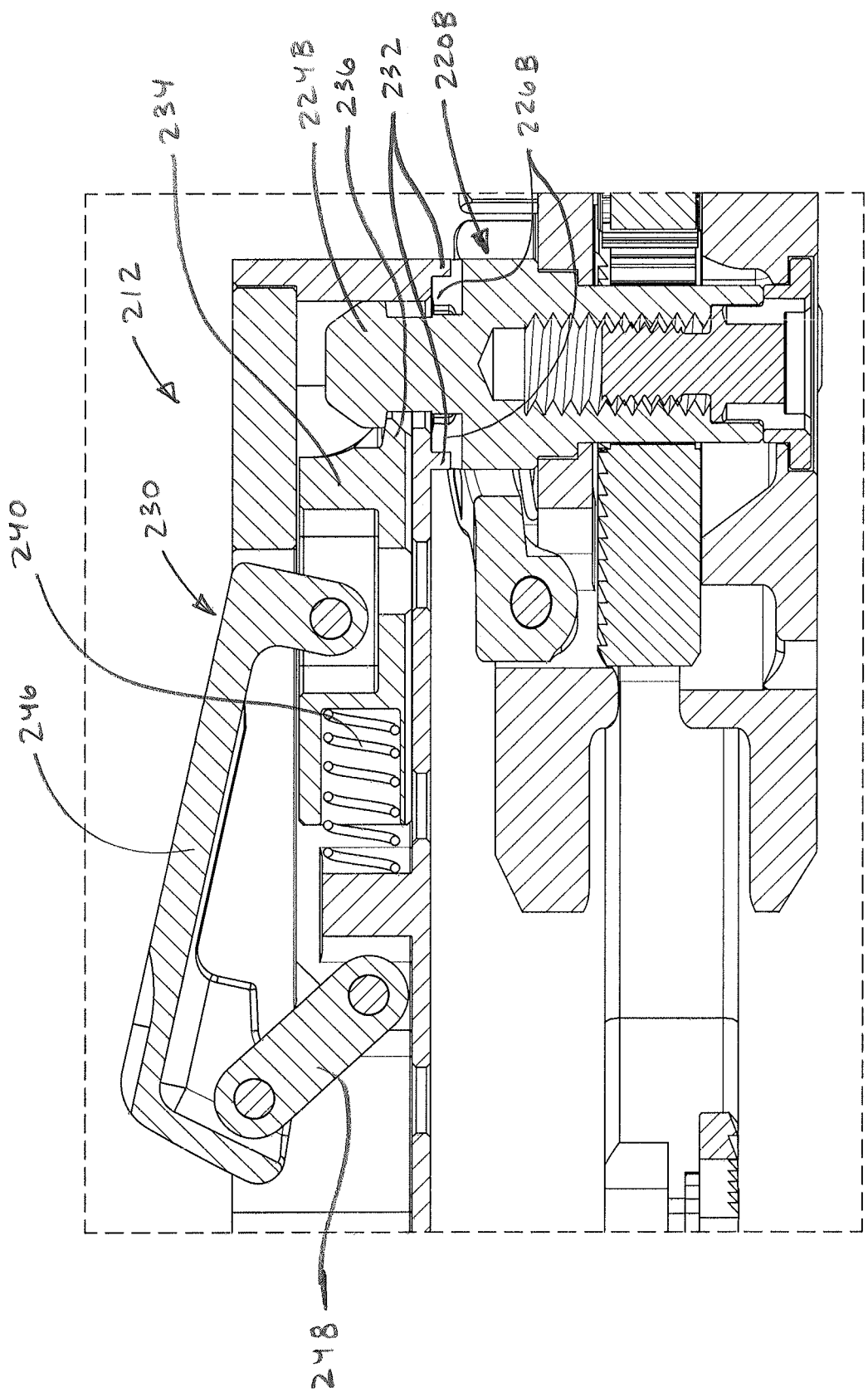
FIG. 26 is an enlarged, fragmentary cross section taken through the actuator adaptor and retractor of FIG. 25.
Figure 27:
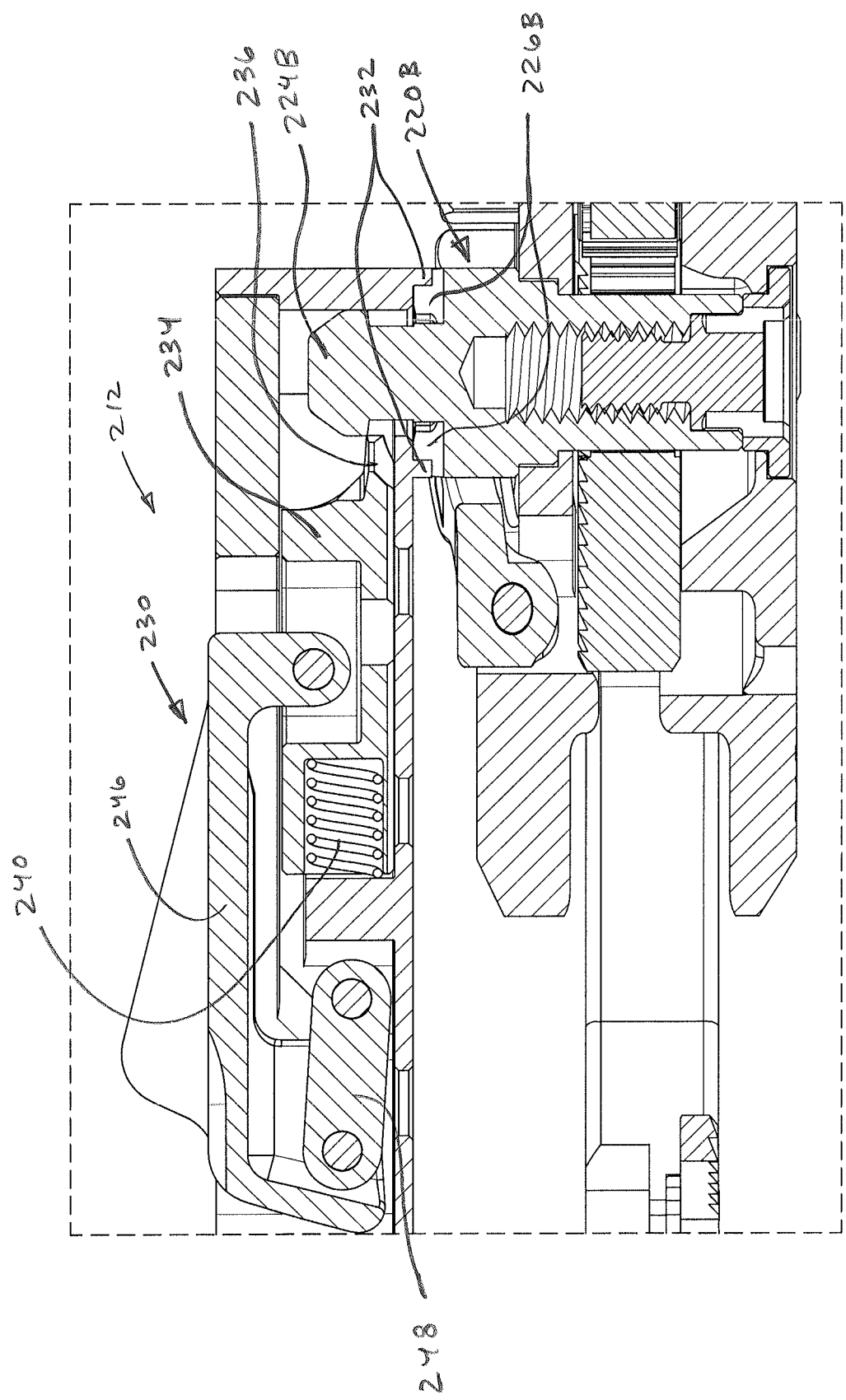
FIG. 27 is similar to FIG. 26, but with the actuator adaptor unlatched.

Referring to FIGS. 24 and 25, the retractor adaptor 212 includes an elongate adaptor body 230 having proximal and distal ends. The proximal end of the adaptor body 230 is internally threaded to threadably mate with the coupler 216. The distal end of the body 230 has a lower end including an annular row of teeth 232 configured to mesh and engage the annular row of teeth 226A, 226B of the adaptor mounts 220A, 220B. Referring to FIGS. 26 and 27, the retractor adaptor 212 further includes a latch, generally indicated at 230 configured to releasably latch the adaptor on the stud 224A, 224B. The latch 230 includes a retractable plunger 234 having an arcuate claw 236. The plunger 234 is selectively movable between a latched position, in which the arcuate claw 236 is moved under the button head of the button stud 224A, 224B and inhibits the adaptor 212 from being removed from the stud, and an unlatched position, in which the arcuate claw is disengaged from the button head and enables the adaptor to be removed from the stud.

Referring still to FIGS. 26 and 27, the latch 230 further includes a spring 240 biasing the plunger 234 in the latched position, and a release mechanism configured to enable the plunger to be moved to the unlatched position against the bias of the spring 240. The release mechanism includes a button 246 having one end hingedly coupled to the plunger 234 and an opposite end hingedly coupled to one end of a connecting link 248. The other end of the connecting link 248 is hingedly coupled to the adaptor body 230. In operation, the button 246 is pushed downward so that it rotates about its hinged connection to the plunger, thereby causing the plunger to slide and retract proximally relative to the adaptor body 230. In generally, the release mechanism 242 operates as a slider-crank mechanism, whereby the button 246 functions as the connecting rod, the connecting link functions as the crank (although the crank does not actuate the slider-crank), and the plunger functions as the slider.

In use, the retractor adaptor 212 is positioned over one of the adaptor mounts 220A, 220B in a selected angular position relative to the retractor 10. The adaptor 212 is then latched onto the selected adaptor mount 220A, 220B in the selected angular position, such that the annular row of teeth 232 of the adaptor 212 mesh with the annular row of teeth 226A, 226B of the adaptor mount to inhibit rotation of the adaptor on the adaptor mount. The retractor adaptor 212 is readily removable from the retractor 10 by depressing the button 246 and pulling the adaptor off of the adaptor mount 220A, 220B.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A retractor for spine surgery comprising:
   a body having proximal and distal ends and a longitudinal axis extending between the proximal and distal ends;
   left, right, and center retracting arms coupled to the body and extending distally relative to the body;
   left, right, and center blades operatively coupled to distal ends of the respective retracting arms; and
   left and right springs,
   wherein the left retracting arm is independently rotatable about a left rotational axis to selectively independently move the left blade away from and toward the right blade in a generally lateral direction relative to the longitudinal axis of the body,
   wherein the right retracting arm is independently rotatable about a right rotational axis that is separate and spaced apart from the left rotational axis to selectively independently move the right blade away from and toward the left blade in a generally lateral direction relative to the longitudinal axis of the body,
   wherein each left and right retracting arms are rotatably drivable independently about the respective left and right rotational axes and relative to the body via a corresponding rack and pinion mechanism and a corresponding a lever mechanism,
   wherein each of the left and right retracting arms functions as an effort arm and a load arm of the corresponding lever mechanism,
   wherein the left spring is operatively coupled to the body and the effort arm of the left retracting arm to apply a left biasing force to the effort arm of the left retracting arm, thereby biasing the effort arm of the left retracting arm away from the longitudinal axis and biasing the load arm of the left retracting arm toward the longitudinal axis,
   wherein the right spring is operatively coupled to the body and the effort arm of the right retracting arm to apply a right biasing force to the effort arm of the right retracting arm, thereby biasing the effort arm of the right retracting arm away from the longitudinal axis and biasing the load arm of the right retracting arm toward the longitudinal axis.

2. The retractor set forth in claim 1, wherein the effort arms are configured to nest within the body.

3. The retractor set forth in claim 2, further comprising a ratchet rack fixedly coupled to each effort arm and engaging a pawl coupled to the body.

4. The retractor set forth in claim 1, wherein the center retracting arm is coupled to a rack and pinion mechanism to enable linear movement of the center retracting arm relative to the body.

5. The retractor set forth in claim 4, wherein each of the rack and pinion mechanisms includes a tool coupler at an upper surface of the body, wherein the tool couplers are configured to couple to a tool to actuate rotation of the corresponding pinion.

6. A retractor adaptor configured to couple to a tissue retractor for spine surgery, the retractor adaptor comprising:
   an adaptor body having proximal and distal ends, the proximal end of the adaptor body configured to couple to an arm mount;
   an annular row of teeth at the distal end of the adaptor body configured to mesh with an annular row of teeth of an adaptor mount of the tissue retractor; and
   a latch configured to releasably latch the retractor adaptor on the adaptor mount,
   wherein the latch includes a plunger selectively movable linearly between a latched position and an unlatched position, and a spring biasing the plunger in the latched position.

7. The retractor adaptor set forth in claim 6, further comprising a release mechanism configured to enable the plunger to be moved linearly to the unlatched positon against the bias of the spring.

8. The retractor adaptor set forth in claim 7, wherein the release mechanism includes a depressible button having one end hingedly coupled to the plunger, wherein pushing the button downward moves the latch linearly to the unlatched position against the bias of the spring.

9. The retractor adaptor set forth in claim 6, wherein the latch further operates as a slider-crank mechanism to impart linear movement of the plunger.

10. A retractor assembly for spine surgery comprising:
    a retractor including
       a body having proximal and distal ends and a longitudinal axis extending between the proximal and distal ends,
       retracting arms operatively coupled to the body and extending distally relative to the body,
       blades operatively coupled to distal ends of the respective retracting arms, and
       an adaptor mount coupled to at least one of the body and one of the retracting arms, the adaptor mount including an annular row of teeth, and a stud having an enlarged button head, wherein the annular row of teeth of the adaptor mount surrounds the stud and the stud project upward above the annular row of teeth; and
    a retractor adaptor configured to couple to the retractor, the retractor adaptor including
       an adaptor body having proximal and distal ends, the proximal end of the adaptor body configured to couple to an arm mount,
       an annular row of teeth at the distal end of the adaptor body configured to mesh with the annular row of teeth of the adaptor mount of the retractor, and
       a latch configured to releasably latch the retractor adaptor on the adaptor mount, wherein the latch includes a plunger selectively movable between a latched position and an unlatched position, wherein the plunger includes a claw, wherein the claw is positioned under the enlarged button head of the stud when the plunger is in the latched position, wherein the claw is removed from under the enlarged button head of the stud when the plunger is in the unlatched position.

11. The retractor assembly set forth in claim 10, wherein the retracting arms include a center retractor arm selectively movable along the longitudinal axis of the body, wherein the adaptor mount is coupled to the center retractor arm.

12. The retractor assembly set forth in claim 10, wherein the adaptor mount is coupled to the body of the retractor.

13. The retractor adaptor set forth in claim 10, wherein an entirety of the button head is receivable in the distal end of the adaptor body.

* * * * *